(12) United States Patent
Joseph et al.

(10) Patent No.: US 12,741,088 B2
(45) Date of Patent: Sep. 22, 2026

(54) CONTINUOUS SUBCUTANEOUS INSULIN INFUSION CATHETER

(71) Applicant: THOMAS JEFFERSON UNIVERSITY, Philadelphia, PA (US)

(72) Inventors: Jeffrey I. Joseph, Philadelphia, PA (US); Paul J. Strasma, Irvine, CA (US); Mark A. DeStefano, Collegeville, PA (US); Brian M. Shelton, Altadena, CA (US); Kenneth C. Hsu, Irvine, CA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/928,854

(22) Filed: Mar. 22, 2018

(65) Prior Publication Data

US 2018/0207356 A1 Jul. 26, 2018

Related U.S. Application Data

(63) Continuation of application No. PCT/US2016/053118, filed on Sep. 22, 2016.
(Continued)

(51) Int. Cl.
*A61M 5/158* (2006.01)
*A61M 39/02* (2006.01)
(Continued)

(52) U.S. Cl.
CPC ........ *A61M 5/158* (2013.01); *A61M 25/0045* (2013.01); *A61M 39/0247* (2013.01);
(Continued)

(58) Field of Classification Search
CPC .............. A61M 5/158; A61M 25/0023; A61M 25/0045; A61M 25/005; A61M 25/007;
(Continued)

(56) References Cited

U.S. PATENT DOCUMENTS 5,425,723 A 6/1995 Wang
5,800,407 A 9/1998 Eldor
(Continued)

FOREIGN PATENT DOCUMENTS

WO 2001034237 A1 5/2001
WO WO 2017/125817 7/2017

OTHER PUBLICATIONS

Edsberg B, Herly D, Hildebrandt P, Kuhl C. Insulin bolus given by sprinkler needle: effect on absorption and glycaemic response to a meal. Br Med J (Clin Res Ed). May 30, 1987;294(6584):1373-6.
(Continued)

*Primary Examiner* — James D Ponton
*Assistant Examiner* — John A Doubrava
(74) *Attorney, Agent, or Firm* — Saul Ewing LLP; Kathryn Doyle; Sean J. D.

(57) ABSTRACT

A continuous subcutaneous infusion catheter includes an elongate flexible cannula and a plurality of holes through the cannula wall that are positioned both along the axial length of the cannula and radially around the cannula. The proximal end of the cannula is configured to be attached to a pump, and the distal end of the flexible cannula is atraumatic. The catheter can be used to deliver insulin to a patient.

43 Claims, 40 Drawing Sheets

Related U.S. Application Data

(60) Provisional application No. 62/345,442, filed on Jun. 3, 2016, provisional application No. 62/222,055, filed on Sep. 22, 2015.

(51) Int. Cl.
*A61M 5/32* (2006.01)
*A61M 25/00* (2006.01)
*A61M 25/06* (2006.01)

(52) U.S. Cl.
CPC ............... *A61M 2005/1585* (2013.01); *A61M 2005/1586* (2013.01); *A61M 5/3291* (2013.01); *A61M 25/0023* (2013.01); *A61M 2025/0046* (2013.01); *A61M 25/005* (2013.01); *A61M 25/007* (2013.01); *A61M 25/065* (2013.01); *A61M 2039/0258* (2013.01); *A61M 2039/0273* (2013.01); *A61M 2039/0276* (2013.01); *A61M 2205/582* (2013.01); *A61M 2205/8206* (2013.01)

(58) Field of Classification Search
CPC ...... A61M 25/0065; A61M 2005/1586; A61M 2025/0046; A61M 2205/582; A61M 2205/8206
See application file for complete search history.

(56) References Cited

U.S. PATENT DOCUMENTS 5,848,996 A 12/1998 Eldor
6,042,576 A * 3/2000 DeVries ................ A61M 25/06 604/523
6,179,816 B1 * 1/2001 Mottola ............. A61M 25/007 604/264
6,261,272 B1 7/2001 Gross et al.
6,471,689 B1 * 10/2002 Joseph ................ A61M 5/1723 424/424
6,488,663 B1 12/2002 Steg
7,361,158 B1 * 4/2008 Mooney, Jr. .......... A61M 25/06 604/174
7,588,558 B2 9/2009 Sage, Jr. et al.
7,666,172 B2 2/2010 Atil
7,875,008 B2 1/2011 Chong et al.
8,043,229 B2 10/2011 Mulvihill et al.
8,062,250 B2 11/2011 Mogensen et al.
8,206,343 B2 6/2012 Racz
8,333,734 B2 12/2012 Zohmann
8,403,911 B2 3/2013 Adams et al.
8,708,994 B2 4/2014 Pettis et al.
8,827,979 B2 9/2014 Pesach et al.
9,084,848 B2 7/2015 Schiltges et al.
9,345,857 B2 5/2016 Latere Dwan Isa et al.
9,375,529 B2 6/2016 Searle
9,782,536 B2 10/2017 Skutnik et al.
9,844,631 B2 * 12/2017 Bureau ............. A61M 37/0015
2004/0075198 A1 * 4/2004 Schweikert ....... A61M 25/0009 264/634
2004/0215202 A1 * 10/2004 Preissman .......... A61B 17/8833 606/94
2004/0236290 A1 * 11/2004 Zimmermann ......... A61L 29/16 604/265
2005/0192558 A1 * 9/2005 Bernard ............. A61M 25/007 604/525
2005/0273076 A1 * 12/2005 Beasley ............ A61M 25/0637 604/164.01
2006/0100583 A1 5/2006 Terzoli
2006/0135941 A1 6/2006 Porto et al.
2008/0091173 A1 4/2008 Belley
2008/0269687 A1 10/2008 Chong et al.
2008/0281297 A1 * 11/2008 Pesach ................ A61M 5/1723 604/113
2008/0287877 A1 11/2008 Gresham
2009/0192498 A1 * 7/2009 Andrew .................. A61M 1/89 604/542
2010/0140125 A1 * 6/2010 Mathiasen ............ A61M 5/158 604/174
2011/0099789 A1 * 5/2011 Ewing ..................... A61L 29/08 427/2.25
2012/0078226 A1 * 3/2012 Latere Dwan'isa ......................... A61M 25/007 604/506
2012/0265166 A1 10/2012 Yodfat
2013/0245555 A1 * 9/2013 Dirac .................... A61M 5/158 604/174
2014/0025039 A1 1/2014 Rajendran et al.
2014/0058353 A1 * 2/2014 Politis ............... A61M 5/14248 604/164.04
2015/0051583 A1 * 2/2015 Horvath ............ A61M 25/0015 604/523
2015/0057611 A1 * 2/2015 Bureau ............. A61M 37/0015 604/131
2015/0112302 A1 * 4/2015 Chattaraj ................ A61P 43/00 604/257
2015/0165161 A1 6/2015 Uber, III et al.
2015/0290390 A1 * 10/2015 Ring ................ A61M 5/14216 604/257
2016/0166762 A1 6/2016 Ring et al.
2016/0290390 A1 10/2016 Ambroise et al.
2017/0021127 A1 * 1/2017 Manouchehr ....... A61M 5/3291
2018/0200412 A1 7/2018 Dang

OTHER PUBLICATIONS

Calthorpe N. The history of spinal needles: getting to the point. Anaesthesia. Dec. 2004;59(12):1231-41.

Campolo M, Molin D, Rawal N, Soldati A. Protocols to compare infusion distribution of wound catheters. Med Eng Phys. Apr. 2012;34(3):326-32.

Pfützner A, Raz I, Bitton G, Klonoff D, Nagar R, Hermanns N, et al. Improved Insulin Absorption by Means of Standardized Injection Site Modulation Results in a Safer and More Efficient Prandial Insulin Treatment. A Review of the Existing Clinical Data. J Diabetes Sci Technol. Jan. 2015,9(1):116-22.

International Search Report of PCTUS16/53118 dated Feb. 16, 2017.

European Search Report issued in corresponding European Patent Application No. 16849597.6 on May 14, 2019.

Ramanathan, S., et al., "Single Orifice Soft-tip Catheters vs Multi-orifice Firm-tip Catheters for Epidural Labor Analgesia", In the Proceeding of the International Anesthesia Research Society; 73rd Clinical and Scientific Congress, Los Angeles, CA; Mar. 12-16, 1999: Obstetric Anesthesia, 6 pages.

Toledano, R. D., et al., "Epidural Catheter Design, History, Innovations, and Clinical Implications", Anesthesiology, V 121, No. 1, Jul. 2014, 9 pages.

* cited by examiner 1400
1491

2203
2200
2205
2201

2303
2300
2305
2301
2307

2603
2600
2601
2607
2605

2703
2700
2701
2707
2705

CONTINUOUS SUBCUTANEOUS INSULIN INFUSION CATHETER

CROSS REFERENCE TO RELATED APPLICATIONS

This application is a continuation under 35 U.S.C. 111(a) of International Application No. PCT/US16/53118, filed Sep. 22, 2016, which claims priority to U.S. Provisional Patent Application No. 62/222,055, filed Sep. 22, 2015, titled "CONTINUOUS SUBCUTANEOUS INSULIN INFUSION CATHETER," and U.S. Provisional Patent Application No. 62/345,442, filed Jun. 3, 2016 and titled "CONTINUOUS SUBCUTANEOUS INSULIN INFUSION CATHETER," both of which are incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Approximately 1.2 million people in the United States have type 1 diabetes (T1DM) and require insulin for survival. At least half of these patients use an insulin pump, a continuous subcutaneous insulin infusion (CSII) catheter, and rapid acting insulin to manage their diabetes. The insulin infusion pump produces a pressure differential between the inside of the CSII catheter and the outside of the CSII catheter and the surrounding tissue. Current CSII catheters deliver insulin into the tissue adjacent to the distal tip. The pressure differential causes insulin to flow into the adjacent connective tissue planes along the path of least resistance.

Insulin infused into the subcutaneous tissue surrounding a CSII catheter is absorbed into the circulation through adjacent capillary and lymph vessels. The rate of insulin absorption into the circulation (PK) is closely related to the surface area of insulin in close proximity to capillaries, and the rate of local capillary blood flow. The rate of insulin absorption is also related to the surface area of insulin in close proximity to functioning lymphatic vessels. Insulin can enter the circulation via fenestrated capillaries located within adjacent lymph nodes (fast) or by traveling through multiple lymph nodes and the thoracic duct (slow). Some insulin molecules may be degraded by protease enzymes located within the adjacent inflammatory tissue or lymph nodes prior to entering the circulation.

Further, insulin absorption using current commercial CSII catheters is slow, variable, and unreliable after 2 to 3 days of clinical use. Variable insulin absorption into the bloodstream may be due to variable exposure of insulin to functioning capillary & lymph vessels (surface area), variable capillary blood flow, variable movement across the endothelial cells, variable flow into the lymph vessels, variable degradation within the local lymph nodes, variable capillary absorption within the local lymph nodes, variable insulin degradation within the surrounding tissue, and variable upward movement of insulin onto the skin surface.

Insertion of a CSII cannula through the epidermis, dermis, and subcutaneous tissue damages cells, connective tissue, extra-cellular matrix, arterioles, capillaries, venuoles, and lymphatics. Tissue damage occurs at the time of CSII needle/cannula insertion and may worsen over time due to acute inflammation and ongoing cannula motion. Neutrophils, macrophages, and fibroblasts migrate into the wound. A layer of thrombus and inflammatory tissue forms around the CSII cannula. The layer of inflammatory tissue that surrounds the CSII cannula tends to become thicker and denser the longer the cannula remains within the subcutaneous tissue. However, a layer of inflammatory tissue that is thick, dense, and/or continuous can function as a mechanical barrier to insulin absorption. Some insulin molecules may become trapped within the layer of inflammatory tissue and be degraded by proteases. Some insulin may travel upward along the cannula into more superficial septae. A dense layer of surrounding tissue may force a portion of the insulin bolus upward on the skin surface. Insulin flowing into the subcutaneous tissue layer immediately below the dermis may be absorbed more rapidly because this region has a high density of capillary and lymph vessels. Leakage of insulin onto the skin surface may be a significant cause of variable PK-PD when using insulin pump therapy with a commercial CSII catheter.

An insulin pump produces a hydrostatic pressure differential between the inside of the CSII cannula (orifices or holes) and the adjacent subcutaneous tissue. The subcutaneous tissue immediately adjacent to the CSII cannula's orifices has a heterogeneous composition, structure, and compliance. The layer of inflammatory tissue is highly heterogeneous in composition, structure, and compliance. Thus, the surrounding subcutaneous tissue/layer of inflammatory tissue will produce a variable resistance to the flow of insulin into the adjacent connective tissue septae (back pressure). A larger pressure differential occurs when an insulin pump infuses a meal bolus of insulin (for example 7 units=70 ul) at a rapid rate (for example 10 ul/second) into the adjacent subcutaneous tissue. This type of insulin bolus distends the surrounding layer of inflammatory tissue (causing an increase in back-pressure). Insulin travels through the weakest section of the layer of inflammatory tissue, along the path of least resistance into adjacent loose connective tissue septae (membranous CT made of collagen, elastin, hyaluronan and fibronectin). Thin connective tissue septae divides the adipose cells into lobules and thicker septae surrounds blood vessels, lymph vessels and nerves. A meal bolus of insulin will distend several of the adjacent connective tissue septae, forcing insulin into septae further away from the cannula orifices along paths of least resistance. That is, a meal bolus of insulin infused through a commercial CSII cannula with a single distal orifice will produce a "lake" or "depot" of insulin solution that distends the adjacent connective tissue septae. A sphere-shaped "depot" will produce the least surface area of insulin molecules in contact with vascular tissue. Insulin molecules located in the middle of the "depot" will not be near capillary or lymph vessels, while insulin located on the periphery of the "depot" will be absorbed more rapidly into the circulation.

As a result of the inefficiencies of currently available CSII catheters, patients usually change commercial CSII catheter infusion sites every 2-3 days, each requiring a fresh needle stick (120-180 catheters/year).

There is thus a great clinical need for a CSII catheter that can increase the rate and precision of insulin absorption from the subcutaneous tissue into the circulation for a prolonged period of time (e.g., between 1-30 or 3-28 days).

SUMMARY

In general, in one embodiment, a continuous subcutaneous infusion catheter includes an elongate flexible cannula having a cannula wall and a proximal end and a distal end. The catheter further includes a plurality of holes through the cannula wall that are positioned along an axial length and radially around the cannula. The proximal end of the cannula is configured to be attached to a pump, and the distal end of the flexible cannula is substantially atraumatic.

This and other embodiments can include one or more of the following features. The catheter can further include an introducer having a sharp needle configured to surround the cannula and to pass through skin and subcutaneous tissue. The needle can be 2 mm in length or less. The holes can increase in diameter from the proximal end to the distal end. The distal end can include a self-closing valve configured to allow a stylet to pass therethrough. The cannula can include a lumen therein. The stylet can be configured to extend within the lumen. A proximal-most 1 mm to 2 mm portion of the cannula may not include any holes. The holes can extend along an axial length of the cannula that can be approximately 4 to 12 mm long. The cannula can be configured to contract axially upon insertion. The cannula wall can include an accordion feature. The catheter can further include an external platform that contains a battery powered mechanism configured to vibrate the elongate tube in an up/down, rotational, or side-to-side motion. The vibration can be timed so as to indicate to a user when insulin has been delivered. The catheter can further include a heating mechanism configured to heat the cannula. The catheter can further include an adhesive patch connected to the cannula. The adhesive patch can be configured to attach to skin to hold the cannula in subcutaneous tissue, wherein adhesive on the patch can extend radially all the way to the cannula. The adhesive patch can include a stronger adhesive on an inner ⅓ of the adhesive patch than an outer ⅔ of the adhesive patch. The cannula can further include a mandrel therein configured to aid in moving the cannula through tissue.

In general, in one embodiment, a method of delivering insulin with a continuous subcutaneous infusion catheter includes: (1) inserting a flexible cannula into subcutaneous tissue, where the cannula includes a plurality of holes extending through a cannula wall along a length of the cannula; and (2) pumping insulin through the plurality of holes such that the insulin spreads to the subcutaneous tissue in a substantially cylindrical pattern along the length of the cannula.

This and other embodiments can include one or more of the following features. The method can further include inserting a sharp outer introducer 1-2 mm through epidermis and dermis before inserting the flexible cannula. Inserting the flexible cannula can include inserting the flexible cannula through a lumen of the sharp outer introducer. The method can further include inserting a sharp inner needle through the flexible cannula to pierce through the subcutaneous tissue. The method can further include removing the sharp inner needle from the flexible cannula. The method can further include leaving the cannula in the subcutaneous tissue for more than 2 days. The method can further include leaving the cannula in the subcutaneous tissue for more than 5 days. The insulin can contact a lateral surface area of subcutaneous tissue of over 500 $\mu m^2$. The insulin can contact a lateral surface area of subcutaneous tissue of over 1,000 $\mu m^2$.

In general, in one embodiment, a continuous subcutaneous infusion catheter includes a cannula having a cannula wall and a proximal end and a distal end. The length of the cannula is greater than 2 mm. The catheter further includes a plurality of orifices in the cannula wall and an introducer. The introducer surrounds the cannula and includes a sharp needle that is 2 mm or less in length that is configured to pass through epidermis and dermis.

This and other embodiments can include one or more of the following features. The orifices can increase in diameter from a proximal end of the cannula to a distal end of the cannula. The cannula can further include a mandrel configured to aid in moving the cannula through tissue. The distal end of the cannula can include a self-closing valve configured to allow a stylet to pass therethrough. The cannula can include a lumen therein. The stylet is configured to extend within the lumen. A proximal-most 1 mm to 2 mm portion of the cannula may not include any orifices. The orifices can extend along an axial length of the cannula that is approximately 4 to 12 mm long.

In general, in one embodiment, a method of inserting a catheter includes: (1) inserting a sharp outer insertion needle with a sharp cutting tip having a length of less than 2 mm through the epidermis and dermis; (2) inserting a flexible cannula and inner insertion needle through a lumen of the outer insertion needle; and (3) removing the inner insertion needle.

In general, in one embodiment, a continuous subcutaneous infusion catheter includes an elongate flexible cannula with a proximal end and a distal end. The cannula is smaller than 27 gauge. A plurality of holes extend through the cannula wall along an axial length of the elongate cannula. The proximal end of the cannula is configured to be attached to a pump. The elongate flexible tube includes a reinforcing filament.

These and other embodiments can include one or more of the following features. The reinforcing filament can be a wire or fiber. The reinforcing filament can be made of PTFE. The reinforcing filament can be formed into a braid. The reinforcing filament can be a wire configured to heat up to warm the cannula and adjacent subcutaneous tissue. The reinforcing filament can be configured to vibrate the cannula. The reinforcing filament can be configured to prevent the flexible cannula from kinking. The reinforcing filament can be made of carbon nanotubes or graphene. The holes can increase in diameter from the proximal end to the distal end of the cannula. A proximal-most 1 mm to 2 mm portion of the cannula may not include any holes. The holes can extend along an axial length of the cannula that is approximately 4 to 12 mm long.

In general, in one embodiment, a continuous subcutaneous infusion catheter includes an elongate cannula, a porous scaffold and a plurality of holes extending along the axial length of the cannula. The proximal end is of the cannula configured to be attached to a pump. The porous scaffold is positioned proximate to the proximal end of the cannula. The porous scaffold has a length of less than 100 micrometers.

This and other embodiments can include one or more of the following features. The porous scaffold can include a coating thereon. The scaffold can be biodegradable. The scaffold can be made of Dacron or ePTFE. The scaffold can be configured to facilitate mechanical attachment and ingrowth of epidermis and dermis tissue. The holes can increase in diameter from the proximal end to the distal end of the cannula. A proximal-most 1 mm to 2 mm portion of the cannula may not include any holes. The holes can extend along an axial length of the cannula that is approximately 4 to 12 mm long.

In general, in one embodiment, a continuous subcutaneous infusion catheter includes an elongate cannula, an adhesive patch and a vibration mechanism. The proximal end is of the cannula is configured to be attached to a pump. The elongate cannula has a plurality of holes extending along an axial length thereof. The adhesive patch is configured to attach to the skin to hold the cannula within subcutaneous tissue. The vibration mechanism is configured to vibrate the cannula but not the adhesive patch.

This and other embodiments can include one or more of the following features. The vibration mechanism can include at least one magnet attached to the elongate tube and a coil in contact with the magnet. The catheter can further include an infusion set cap surrounding the elongate tube and can be configured to adhere to a patient's skin. The infusion set cap can be separated from the elongate tube by a flexible member. The flexible member can be a flexible membrane or a flexible arm. The vibration mechanism can be configured to be activated continuously or intermittently. The vibration mechanism can be configured to be activated based upon readings from a sensor. The sensor can be a flow sensor, a pressure sensor, a temperature sensor, or an insulin sensor. The vibration mechanism can includes a piezo-electric element, a coin-cell vibrator, a linear-resonant-actuator, a brushed vibration motor, a brushless vibration motor, or a voice coil actuator. The vibration mechanism can further be configured to heat the cannula.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7 shows the valve closed such that fluid (e.g., insulin) is restricted from passing out of the cannula lumen. FIG. 8 shows the valve open with an introducer needle extending through the cannula lumen and valve.

DETAILED DESCRIPTION

Described herein are continuous subcutaneous infusion catheters, such as continuous subcutaneous insulin infusion (CSII) catheters that enable patients with diabetes to improve their blood glucose control. The infusion catheters described herein can both increase the duration of clinical use and improve the rate and precision of drug (e.g., insulin) absorption by distributing the infusion into a large volume of vascular tissue. Further, the infusion catheters can include a substantially atraumatic needle tip that results in less tissue trauma and inflammation, contributing to more rapid and precise drug absorption from the subcutaneous tissue into the circulation for an extended period of time (e.g., 1-30 days, such as 3-28 days).

Figure 1:
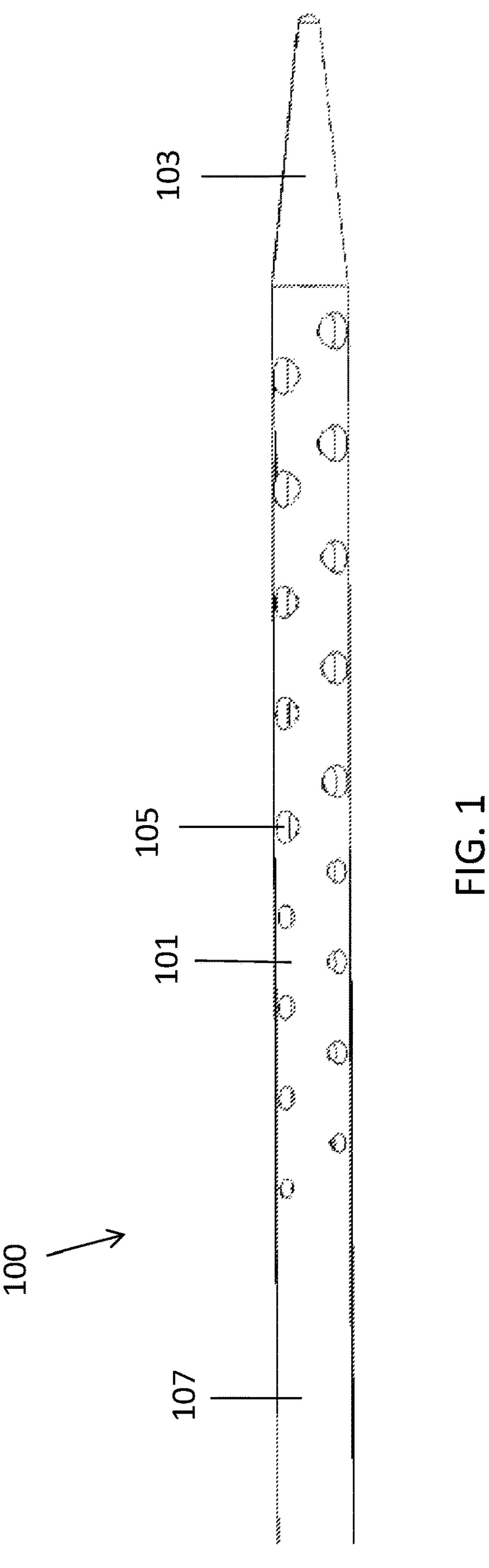
FIG. 1 shows a subcutaneous infusion cannula with a non-traumatic needle tip and multiple holes (orifices) of varying diameter distributed along the sidewall of the cannula.

Referring to FIG. 1, a cannula 100 of a subcutaneous infusion catheter system can include an elongated shaft 101 and a tip 103. The shaft 101 can include one, two or multiple holes (orifices) 105 through the catheter wall. Further, the holes 105 can extend as an array down the axial length (such as approximately 3-10 mm, e.g., 4-6 mm in length) and/or around the circumference of the shaft 101. As shown in FIG. 1, as the holes 105 get closer to the tip 103 and further away from the proximal end 107 of the catheter, they can increase in size. For example, the proximal holes can be 10 micrometers in diameter at the proximal end and gradually increase to 200 micrometers along the length of shaft 101 to the distal tip 103. In other embodiments, the holes 105 can decrease in size towards the distal tip 103 and/or the holes 105 can have a relatively constant size along the length of the shaft 101. In some embodiments, the most proximal hole 105 can be positioned, when implanted, such that it is located below the dermal layer of the patient's skin in order to minimize the risk for insulin leakage onto the skin surface.

The hole size and distribution can be optimized to ensure a substantially uniform pressure differential (P1−P2) between the inside of the shaft 101 and adjacent subcutaneous tissue (when implanted) along the entire length of the shaft 101. The pressure differential will depend upon rate of fluid (e.g., insulin) delivered, volume of fluid delivered, compliance of the CSII tubing and shaft, and compliance of the subcutaneous tissue surrounding the holes of the cannula. In some embodiments, pressure in the insulin pump tubing while infusing a \70 μl bolus of insulin can average between 2 and 10 mmHg, though the pressure can rapidly increase above 200 to 600 mmHg during peak infusion and then slowly dissipate over the following 5 to 30 minutes. Further, the subcutaneous tissue pressure can be very low (e.g. minus 2 to plus 3 mmHg). Thus, there can be a large pressure differential between the inside of the shaft 101 and the adjacent tissue (for example P1−P2=200 mmHg−2 mm Hg=198 mm Hg). In some embodiments, the resistance to flow into adjacent subcutaneous tissue may increase over time. Further, in some embodiments, there can be a decreased resistance to flow after a set period of time, such as 7 days. In some embodiments, the pressure differential is lower when the insulin bolus is infused through the cannula at a slower rate. Insulin pumps deliver the same volume of insulin (for example 70 ul meal bolus) at very different infusion rates (7 seconds versus 28 seconds, versus 180 seconds versus 240 seconds). The hole size and distribution for the cannula 100 may be customized to optimize its clinical performance for an insulin pump that infuses slowly or rapidly.

In some embodiments, the holes 105 can be positioned in a pattern, e.g., symmetric, helical, radial, and/or circumferential pattern, along the length of the shaft 101. In other embodiments, the holes 105 are randomly along the length of the shaft 101. In some embodiments, and as shown in FIG. 1, the most proximal 1 to 2 mm of the shaft 101 does not have holes therein to minimize the risk for insulin to travel upward from the subcutaneous tissue to the skin surface.

In some embodiments, the holes 105 can be distributed in 1, 2, 3, or 4 vertical columns along the shaft 101. Each vertical column can have 1, 2, 3, 4, 5, 6, 7 or 8 holes (i.e. there can be 1 to 32 holes). The distal most holes 105 can be as close to the distal end of the shaft 101 as possible. In some embodiments, laser holes can be drilled at an angle to force the insulin in the downward direction, deeper into the subcutaneous tissue. The holes 105 along the shaft 101 can be staggered to maximize structural support and minimize the risk of kinking. Hole size can vary in diameter from small, medium, large, to larger along the cannula shaft (proximal to distal) for insulin to flow into adjacent tissue in a uniform cylinder pattern.

In some embodiments, the distal tip 103 of the cannula 100 can have a sharp tip that can easily pass through the skin (epidermis and dermis). The needle tip can have sharp edges that cut through the tissue or have more rounded edges (pencil point) that push the tissue out of the way of the advancing cannula in a substantially atraumatic fashion. Substantially atraumatic meaning the tip is designed to reduce trauma and damage to the corresponding tissue. The tip can be made, for example, from a metal (e.g., stainless steel or titanium, carbon nanotubes, a plastic or thermoplastic (e.g., PTFE, polyurethane, polypropylene, polyimide, polycarbonate), or a natural material (e.g., salt, collagen, chitogen). In other embodiments, a separate introducer can be used, as described further below.

In some embodiments, the cannula 100 can be made of a metal (e.g., stainless steel, titanium, nitinol). In other embodiments, the cannula 100 can be made of a plastic, such as PTFE, polyurethane, polypropylene, silicone, or polyimide. The cannula 100 can be rigid or flexible. In some embodiments, the cannula 100 can be finished with a lubricious coating, such as a lubricious silicon coating. In some embodiments, the cannula 100 can be fabricated by laser cutting and welding a hypodermic needle, such as a 27-gauge spinal needle.

Figures 22, 23:
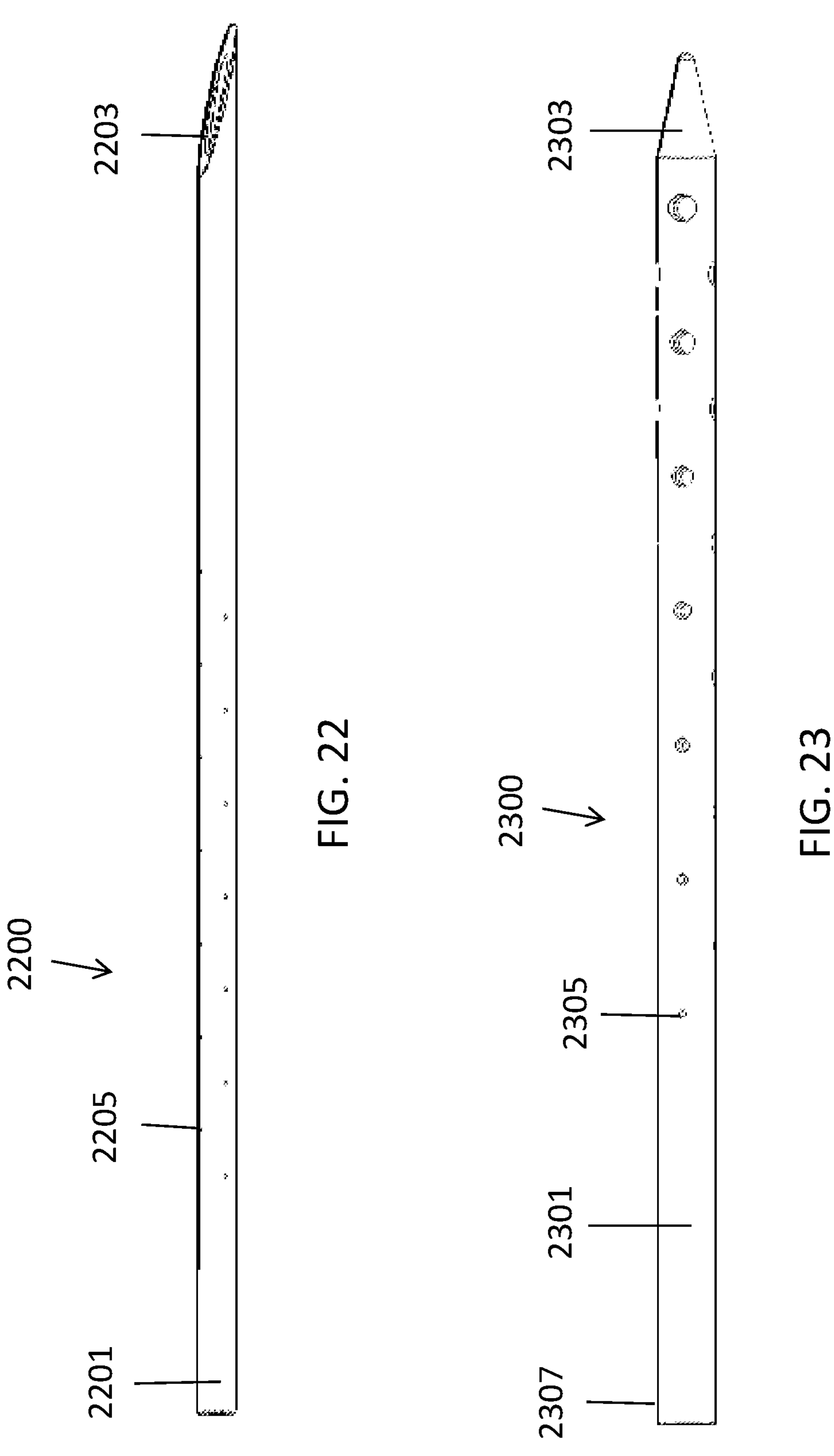
FIG. 22 shows an embodiment of a cannula with holes of uniform size.
FIG. 23 shows an embodiment of a cannula with holes increasing in diameter from the proximal end to the distal end.
Figure 25:
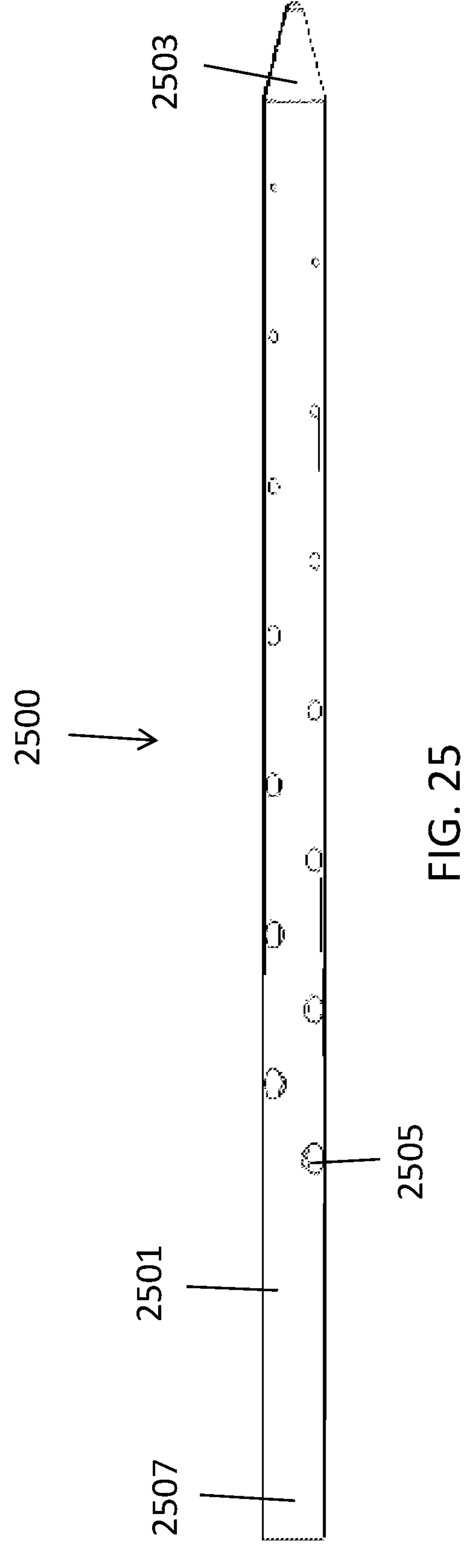
FIG. 25 shows an embodiment of a cannula having holes that decrease in diameter from the proximal end to the distal end.
Figures 26, 27:
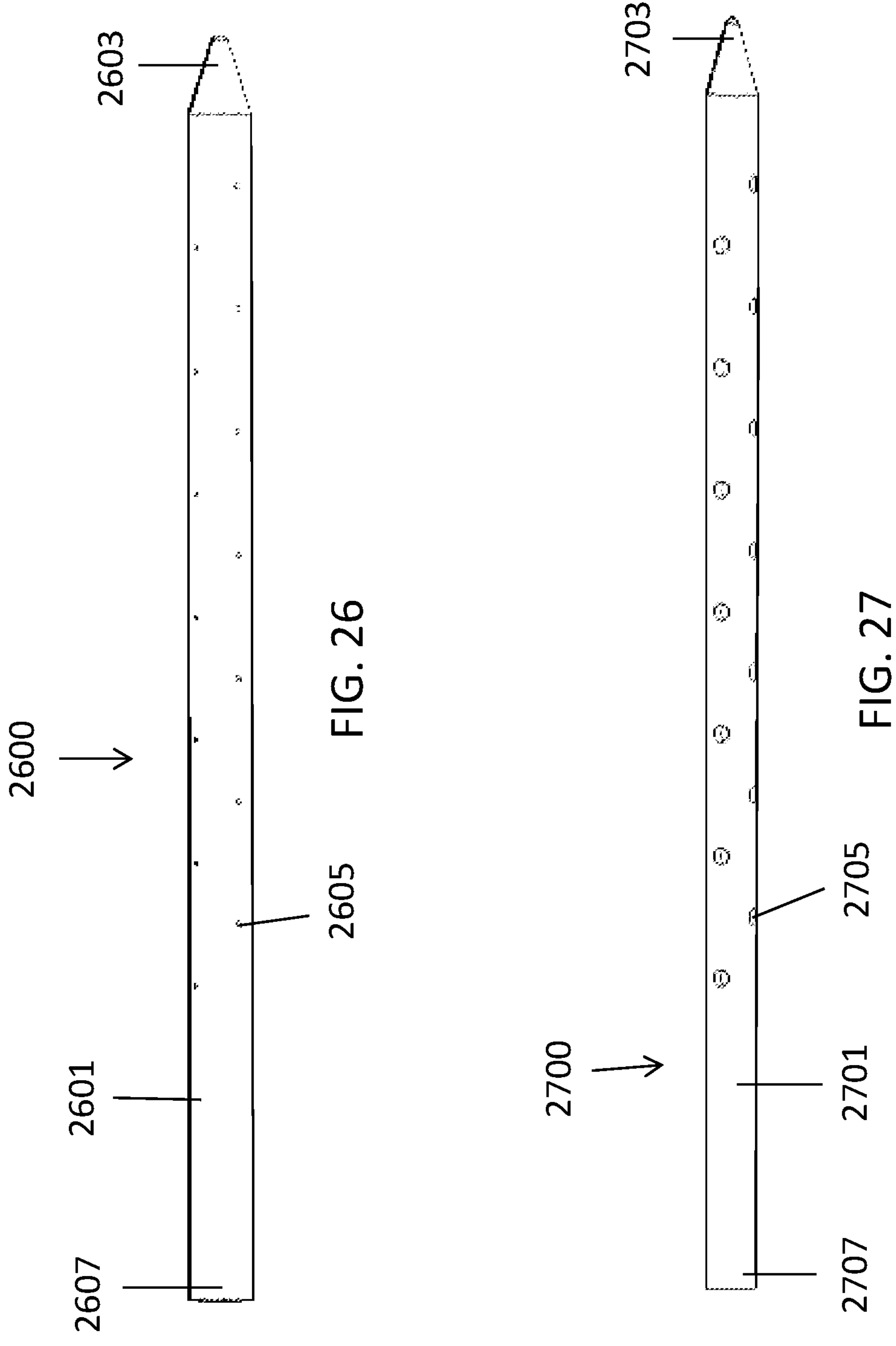
FIG. 26 shows another embodiment of a cannula with holes of uniform size.
FIG. 27 shows another embodiment of a cannula with holes of uniform size.
Figure 28:
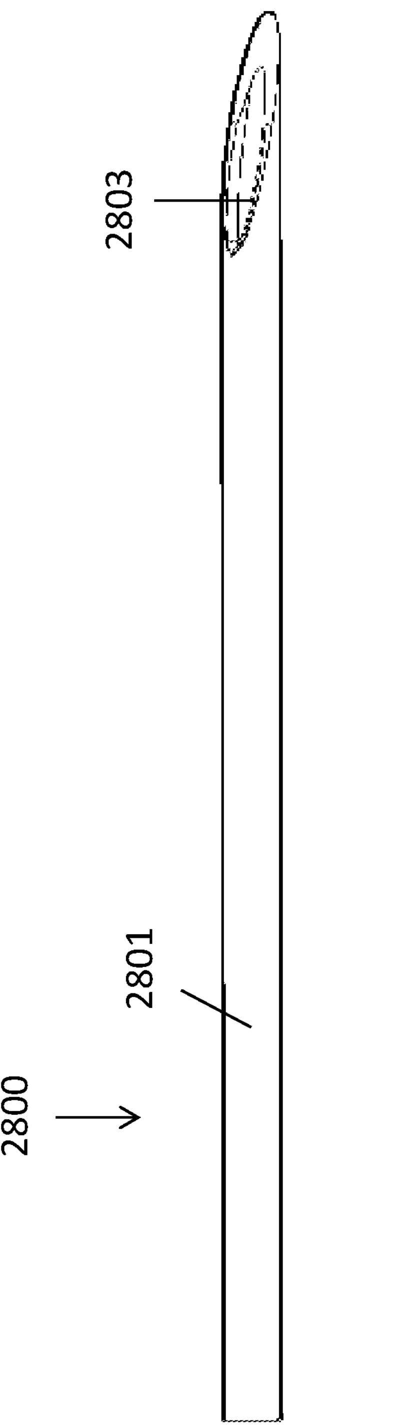
FIG. 28 shows a cannula with a single distal hole.

FIGS. 22-23 and 25-28 show additional embodiments of cannulas that include various combinations of the features of cannula 100. FIG. 22 shows a cannula 2200 having a sharp lancet tip 2203 and holes 2205 of equal size extending down the length of the shaft 2201. For example, the cannula 2200 can be a 27-gauge cannula, and the holes 2205 can have a diameter of 0.005-0.006 inches, such as 0.0056 inches. FIG. 23 shows a cannula 2300 including a pointed but substantially atraumatic tip 2303 and holes 2305 of increasing size from the proximal end 2307 to the tip 2303 of the shaft 2301. For example, the cannula 2300 can be a 27-gauge cannula, and the holes 2305 can increase in size from approximately 0.002" to 0.008" down the length of the shaft 2301. FIG. 25 shows a cannula 2500 having a pointed but substantially atraumatic tip 2503 and holes 2505 of decreasing size from the proximal end 2507 to the tip 2503 of the shaft 2501. For example, the cannula 2500 can be a 27-gauge cannula, and the holes 2505 can decrease in size from approximately 0.008" to 0.002" down the length of the shaft 2501. FIG. 26 shows a cannula 2600 having a pointed but substantially atraumatic tip 2603 and holes 2605 of substantially equal size extending down the length of the shaft 2601. For example, the cannula 2600 can be a 27-gauge cannula with holes of approximately 0.001"-0.002" inches, such as 0.00156 inches in diameter. FIG. 27 shows a cannula 2700 having a pointed but substantially atraumatic tip 2703 and holes 2705 of substantially equal size extending down the length of the shaft 2701. For example, the cannula 2700 can be a 27-gauge cannula with holes of approximately 0.005-0.006 inches, such as 0.00538 inches in diameter. Finally, FIG. 28 shows a cannula 2800 having only a single lumen at the distal tip 2803. Further, the distal tip 2803 can be a sharp beveled lancet tip.

Figure 2:
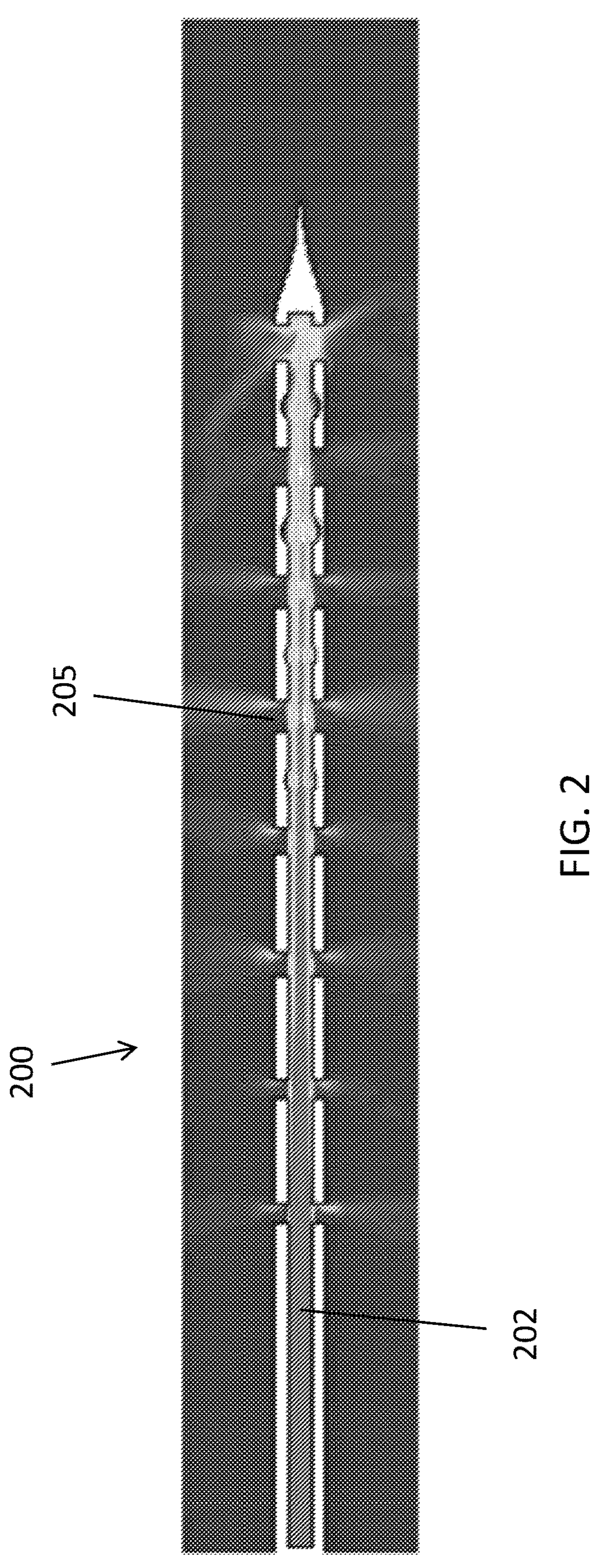
FIG. 2 shows the uniform distribution of flow of non-viscous fluid (e.g., insulin solution) through the holes along the shaft of a cannula.

Referring to FIG. 2, the homogenous distribution of flow of fluid through the cannula 200 into the adjacent subcutaneous tissue can be used to optimize the hole size, distribution pattern, and number of holes. That is, insulin solution will flow through holes 205 of the cannula 200 due to the pressure differential that occurs between the inside and outside of each hole 205 along the path of least resistance. Thus, in some embodiments, if the holes 205 are the same size down the cannula 200, insulin may preferentially flow through the most proximal holes because of the decrease in the cannula lumen hydrostatic pressure distal to the proximal holes. In contrast, as shown in FIG. 2, if the holes 205 increase in size from the proximal end to the distal end, fluid can flow more evenly out of each of the holes 205. As a result, the cannula 200 can have a substantially uniform (e.g., variation within 5-10%) pressure differential and provide uniform distribution of insulin flow into the adjacent vascular tissue (assuming the subcutaneous tissue interstitial fluid hydrostatic pressure is similar from region to region).

Figure 3:
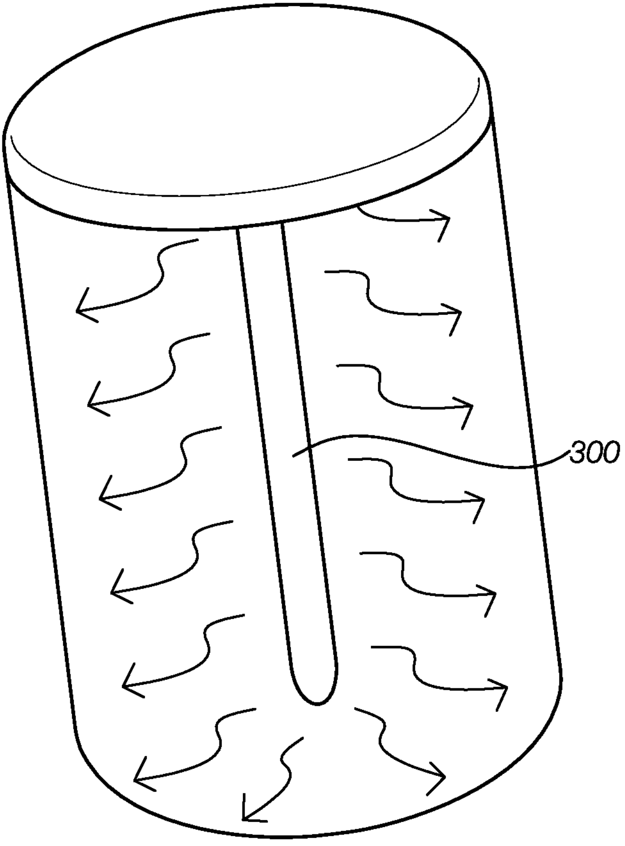
FIG. 3 shows the cylindrical distribution of flow of a non-viscous liquid (e.g., insulin) into the subcutaneous tissue from a continuous subcutaneous catheter as described herein.

As shown in FIG. 3, having multiple holes along the cannula 300 and (and in some embodiments, at an increased size from the proximal to the distal end) can distribute insulin into a larger cylindrical volume of tissue. The cylindrical shape provides a large surface area of insulin-tissue contact or interaction, allowing more access to capillary and lymph vessels and increasing the rate and precision of insulin absorption for an extended period of time (e.g., 1-30, such as 3 to 28 days).

Thus, where a typical 50 μL insulin bolus (e.g., 5 units) for a conventional CSII cannula forms a near-spherical depot with 50 μL volume of fluid contacting a tissue surface area of 65 $\mu m^2$, the infusion catheters described herein can distribute 50 μL volume of insulin along a 4 mm cylinder, providing access to a lateral surface area of 1580 $\mu m^2$. This 24× increase in area of tissue contact will significantly increase the rate and precision of insulin absorption into the adjacent capillary and lymph vessels. Thus, infusing insulin solution through the multiple holes along the sidewall of the cannula and not exclusively at the distal tip will distribute a meal bolus of insulin (50 μl) into a wider area of vascular tissue. Moreover, the rate and precision of insulin absorption using the infusion catheters described herein will be substantially constant. In contrast, infusing the insulin bolus exclusively through a single distal orifice of the cannula that lies adjacent to the most severely damaged tissue (e.g., caused by the needle tip), may decrease the rate and precision of insulin absorption into the blood stream, with increasing insulin absorption variability as the duration of time in the body increases.

In some embodiments, the holes of the cannula can be filled with a material that rapidly dissolves (e.g., sodium chloride-salt) following insertion into the aqueous environment of the subcutaneous tissue. Filing the holes may decrease the resistance to insertion of the cannula into the body, causing less damage to the skin and subcutaneous tissue.

Figure 12:
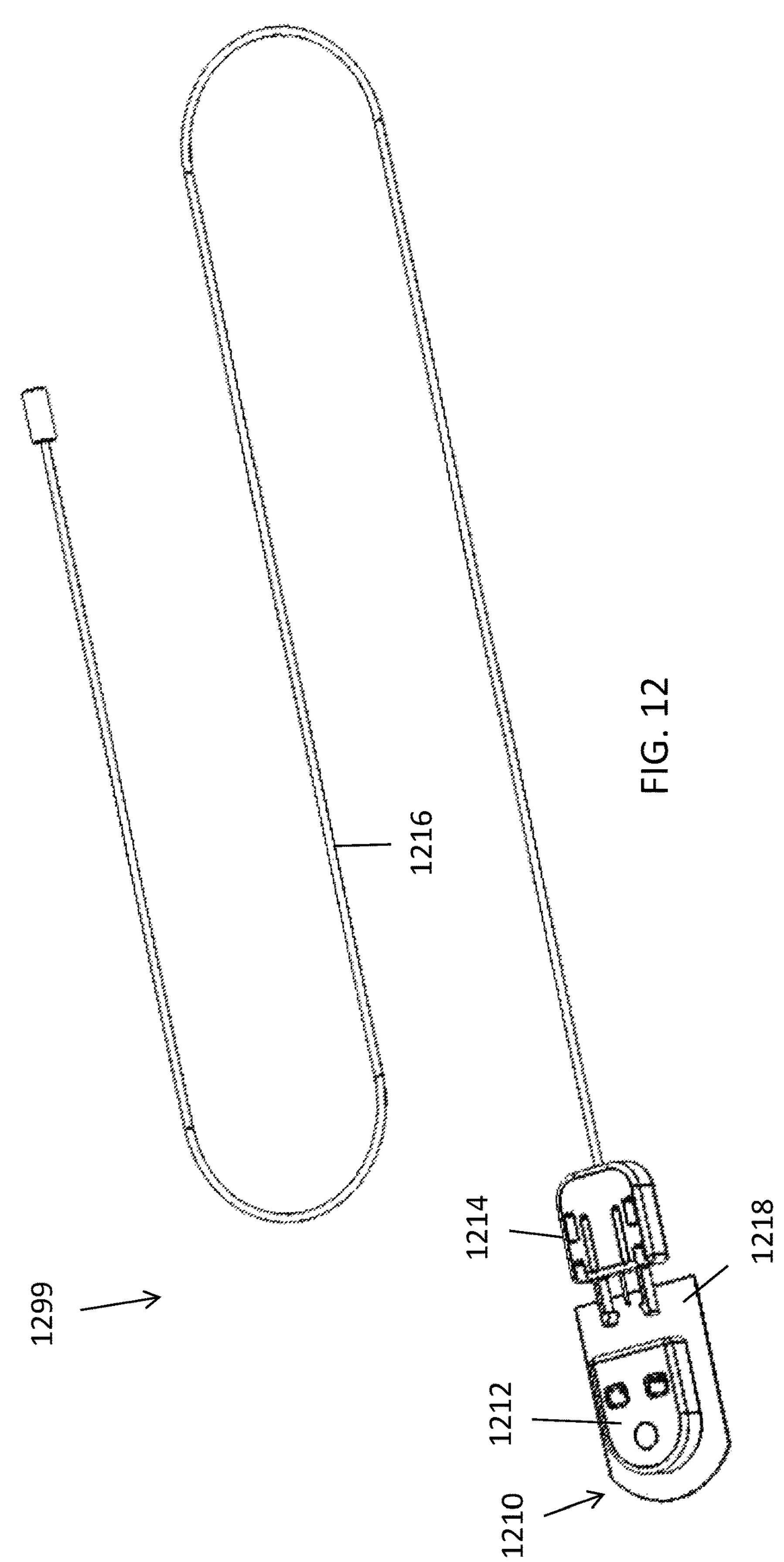
FIGS. 12-13 show a subcutaneous infusion catheter system.
Figure 13:
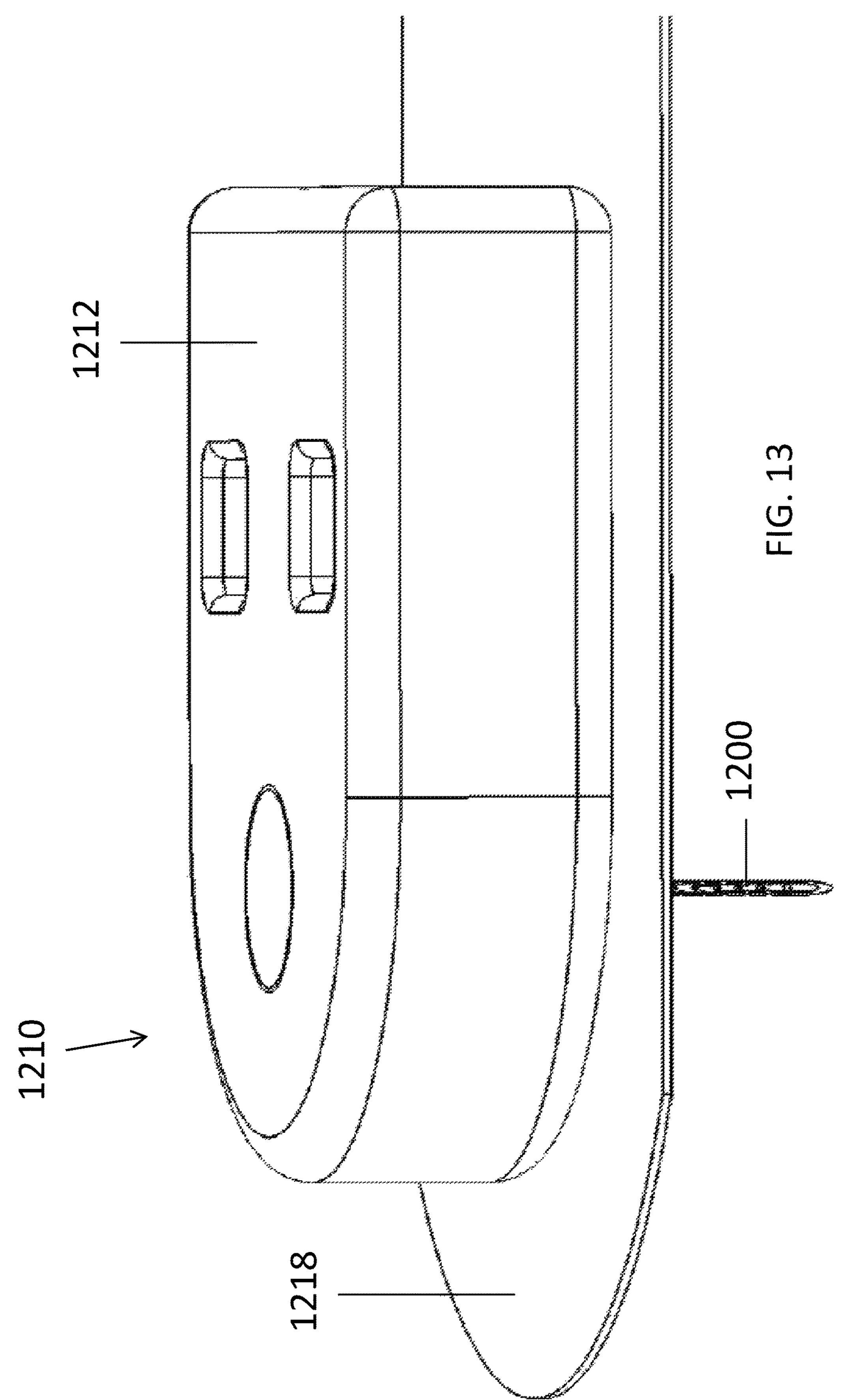
Figure 14A:
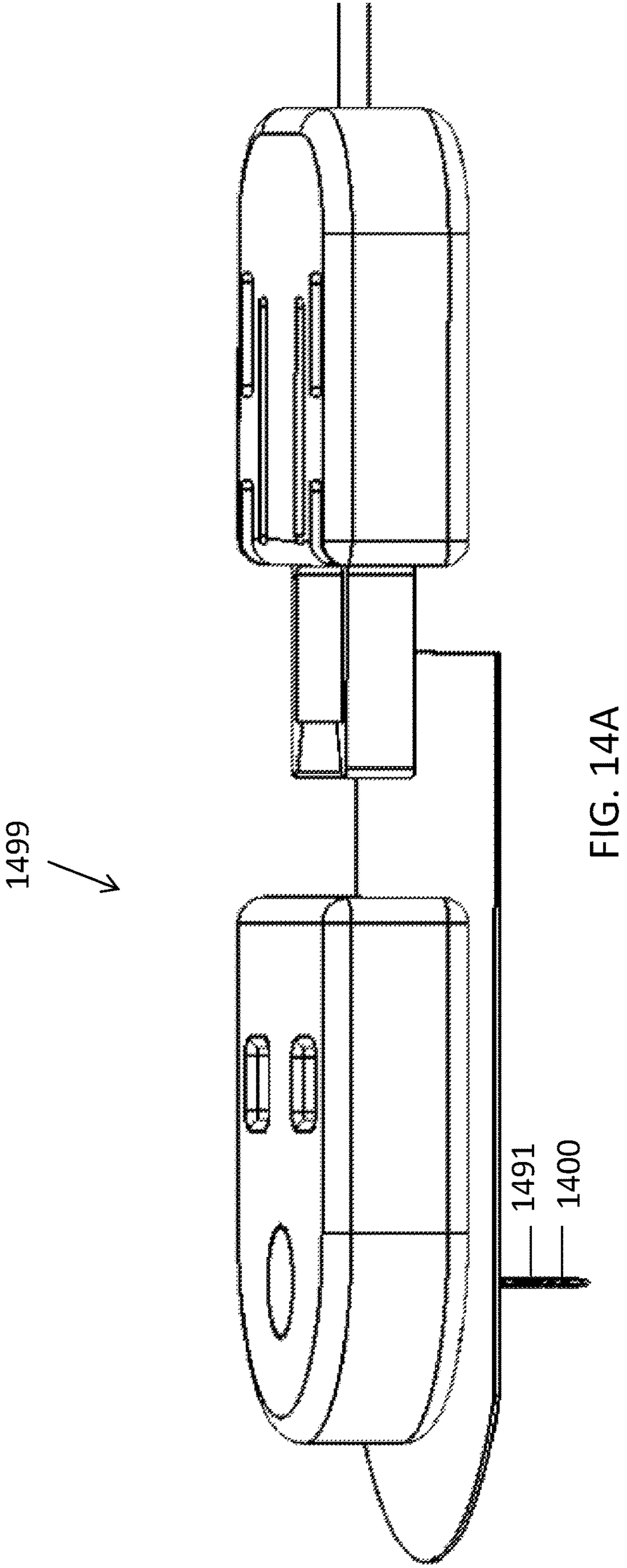
FIGS. 14A-14D show a subcutaneous infusion catheter system with a wire reinforced cannula.
Figure 14B:
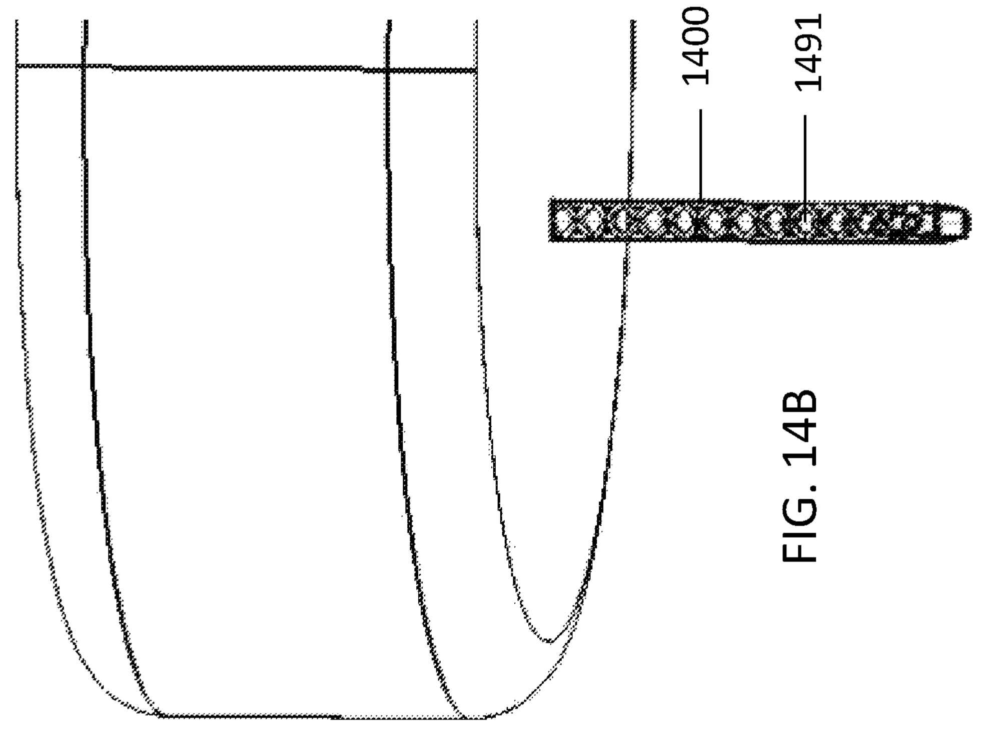
Figure 14C:
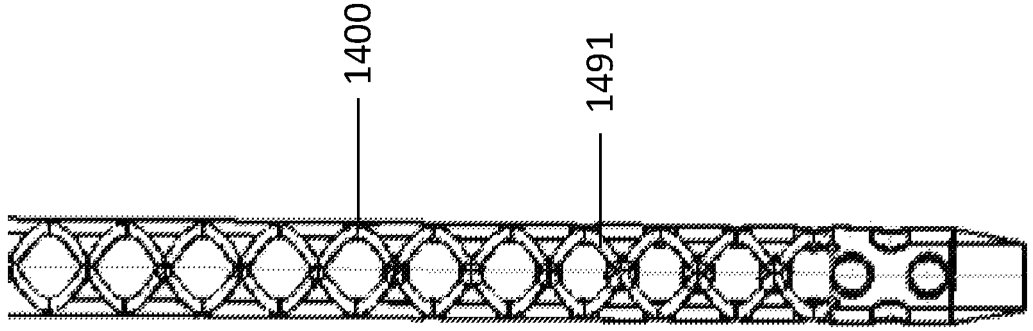
Figure 14D:
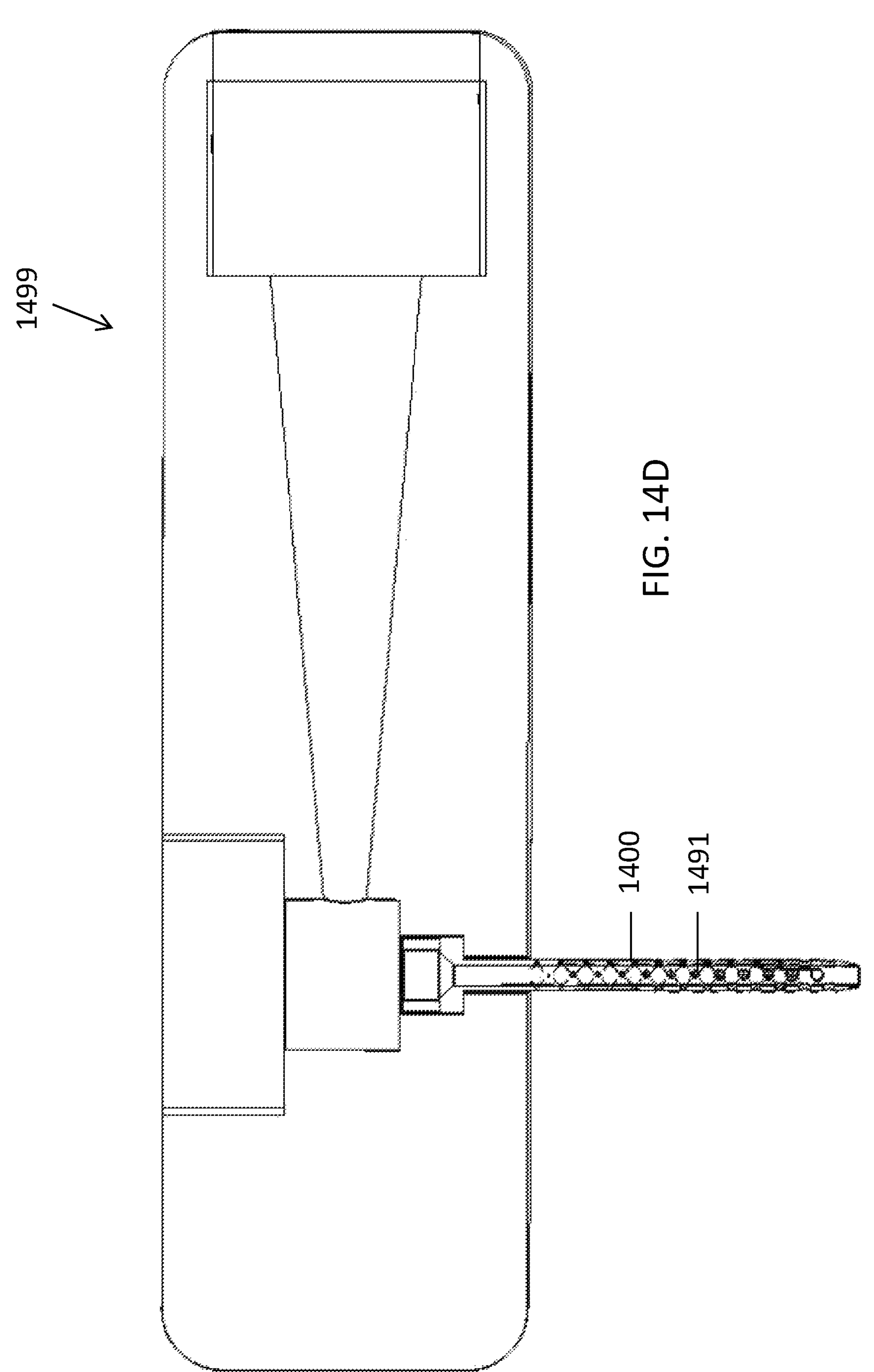

As shown in FIGS. 12-13, the proximal end of the cannula 1200 (similar to cannula 100) can be attached to or integrated with an external platform 1210 as part of a catheter system 1299. The platform 1210 can include an infusion set 1212 configured to hold the battery and electronics therein and a connector 1214. Elongate flexible tubing 1216 can extend from the connector 1214 to an insulin reservoir and pump. The pump can be configured to produce a positive pressure within the cannula 1200 to deliver insulin into the cannula 1200 and the subcutaneous tissue. The external platform 1210 can be configured to quickly connect and disconnect from the tubing 1216 using the connector 1214, which can be a luer lock or pin and clip connection.

Further, an adhesive patch 1218 can hold the platform 1210 to the skin (and thus the catheter 1200 in the subcutaneous tissue). The adhesive patch 1218 can have a wider diameter than the diameter of the base of the platform 1210. A wider surface area of the patch 1218 can increase the strength and mechanical stability of the platform 1210 on the skin surface. The adhesive patch 1218 can be made, for example, of double-sided adhesive tape, and can be configured to hold the platform 1210 securely to the skin surface for at least 7 days. In some embodiments, the adhesive used for the portion of the patch 1218 closest to the cannula (e.g., in the inner ⅓ of the patch 1218) can be stronger than the adhesive on outer portions of the patch 1218 (e.g., the outer ⅔). This can ensure that the cannula 1200 does not piston in/out of the skin and subcutaneous tissue. In some embodiments, benzoin or a similar skin prep chemical can be used to enhance adhesion of the platform 1210 to the skin surface.

The platform 1210 and adhesive patch 1218 can be configured to be gentle on the skin to avoid skin irritation/inflammation that can otherwise occur when using an insulin pump and infusion catheter system for 2 to 4 days or more. Further, the platform 1210, adhesive patch 1218, and any overlying plastic bandage can produce a secure mechanical attachment to the skin that both allows air to reach the skin surface and moisture to wick away.

Figure 4:
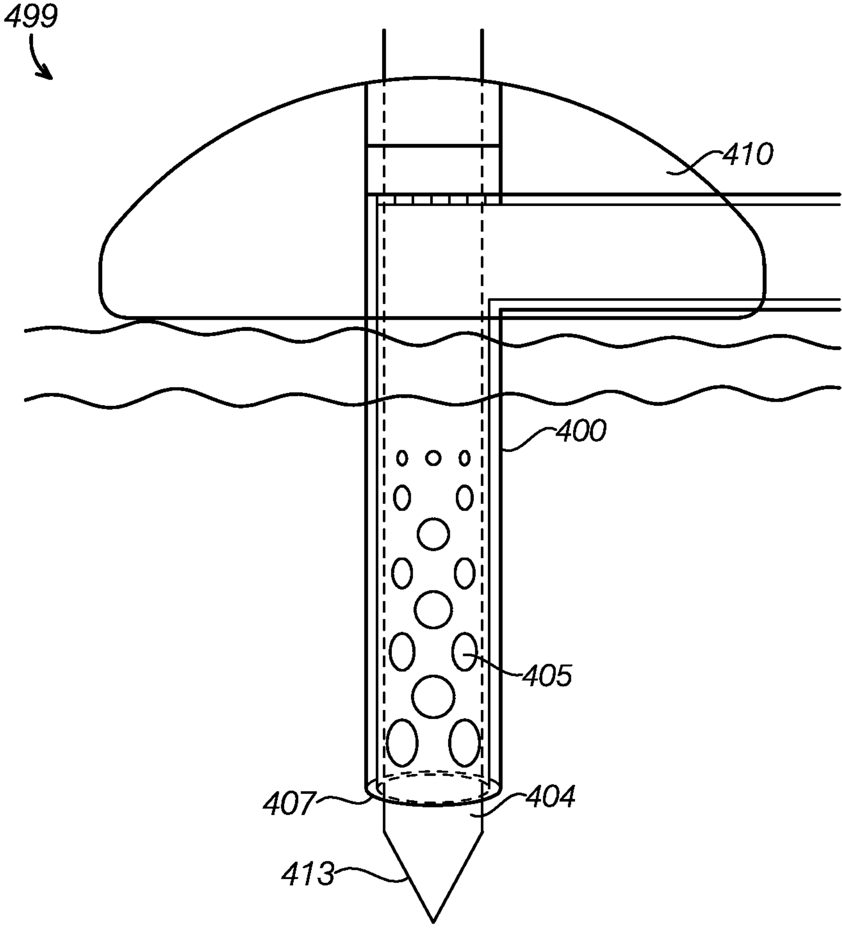
FIG. 4 shows a continuous subcutaneous insulin infusion catheter adhered to the surface of the skin with a removable insertion needle extending through a flexible cannula.

Referring to FIG. 4, in some embodiments, an infusion catheter system 499 can include a platform 410, cannula 400, and insertion needle 404. The insertion needle 404 can include a distal needle tip 413 that extends through the lumen of the cannula 400 and out of a distal orifice 407. The insertion needle 404 can advantageously be used to pierce through the skin (epidermis and dermis), but can then be removed to reduce tissue damage. The cannula 400 can include similar holes 405 as described with respect to the other cannulas described herein. The distal orifice 407 of the cannula 400 may be configured to close off once the insertion needle 404 is removed, as described further below.

Figure 5A:
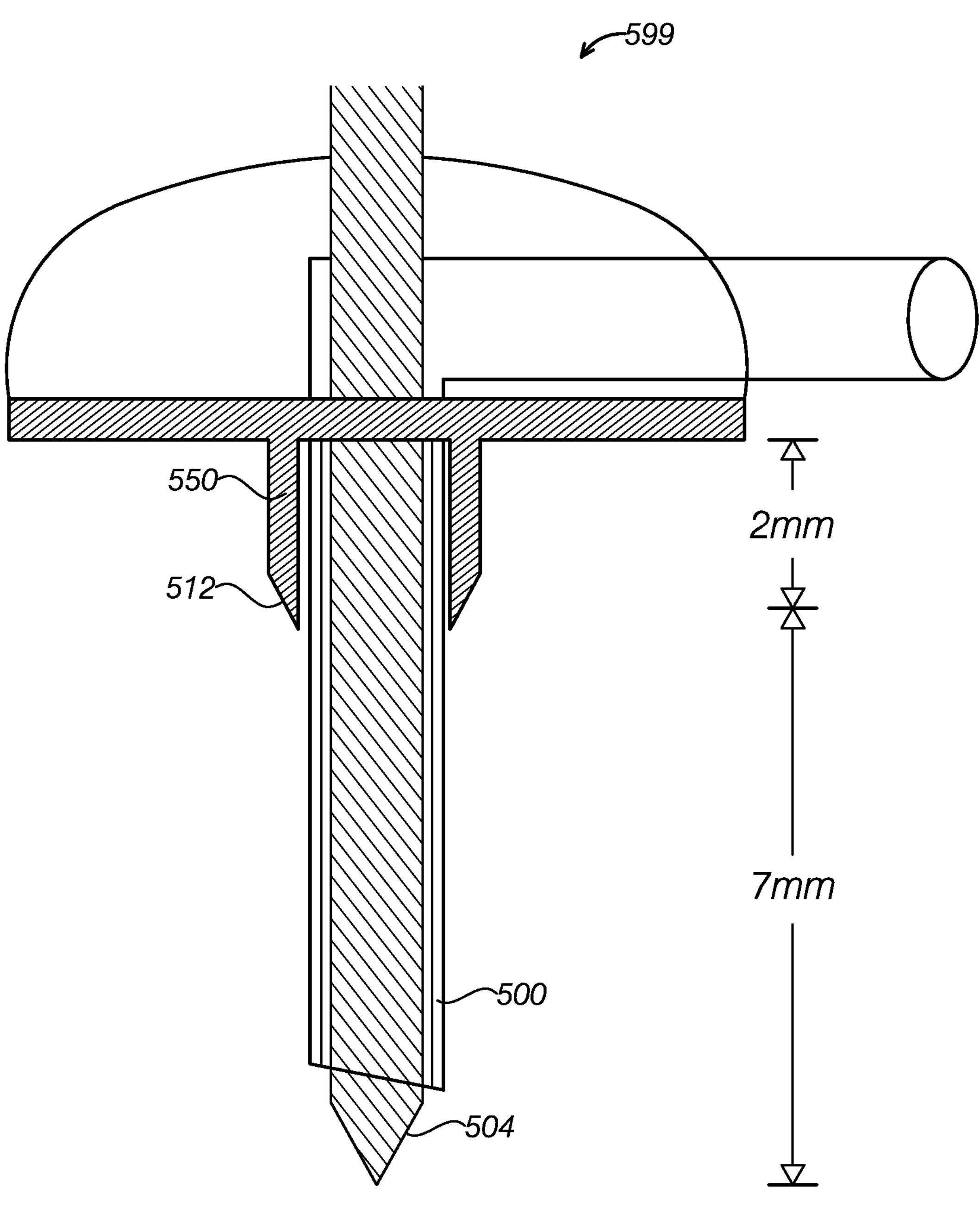
FIGS. 5A-5C show various views of a continuous subcutaneous infusion catheter with an outer introducer needle for making an entrance pathway through the skin (epidermis and dermis) and superficial subcutaneous tissue, a middle flexible cannula with one or more orifices for fluid delivery, and an inner small diameter needle that extends into the subcutaneous tissue.
Figure 5B:
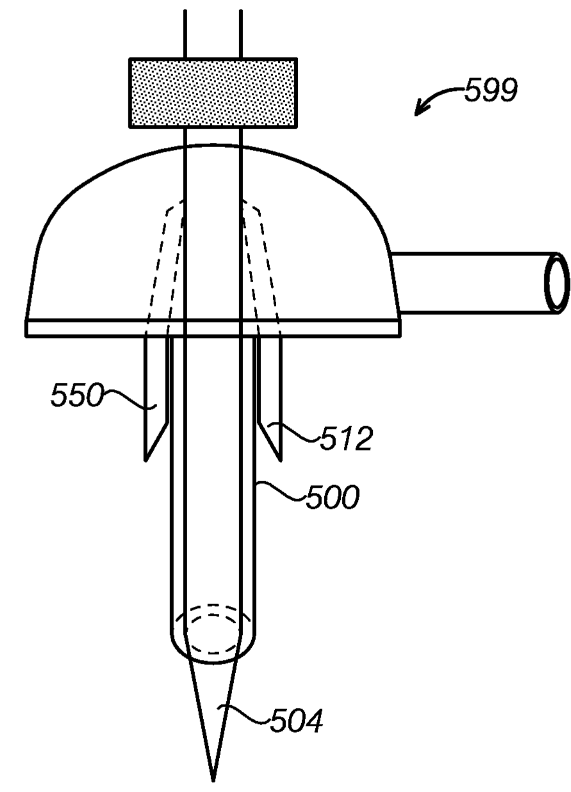
Figure 5C:
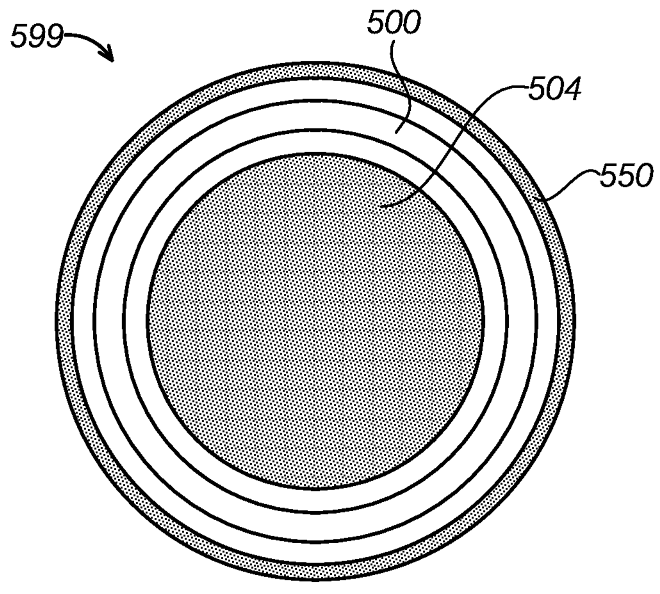

Referring to FIGS. 5A-5C, in some embodiments, an infusion catheter system 599 can include a 1 to 2 mm stylet or outer introducer 550 with a sharp tip 512 and a lumen extending therethrough. The outer introducer 550 can be configured to pierce the skin (epidermis and dermis) only, and then the cannula 500 and needle 504 can be inserted through the lumen of the outer introducer 550. The sharp tip 512 of the introducer 550 can be straight or beveled. Further, in some embodiments, the tip 512 can be a complete circle-shape or a C-shape to allow the tissue of the epidermis and dermis to remain attached to the adjacent skin edge.

Advantageously, the outer introducer 550 can provide a low resistance pathway through the dense tissue of the epidermis and dermis without piercing all the way through the subcutaneous tissue. Further, by having the outer introducer 550, the tip of the introducer needle 504 can be non-cutting (rounded, substantially atraumatic, or blunt like a pencil point) and very small diameter, resulting in a substantially atraumatic insertion, having less damage to the deeper subcutaneous tissue at the time of insertion. In some embodiments, the introducer 550 can be housed within the external platform 510 of the system 599. Although shown in FIGS. 5A-5C as being used with a separate cannula 500 and needle 504, the outer/introducer needle 550 can also be used with a combined cannula/needle tip.

Figure 6A:
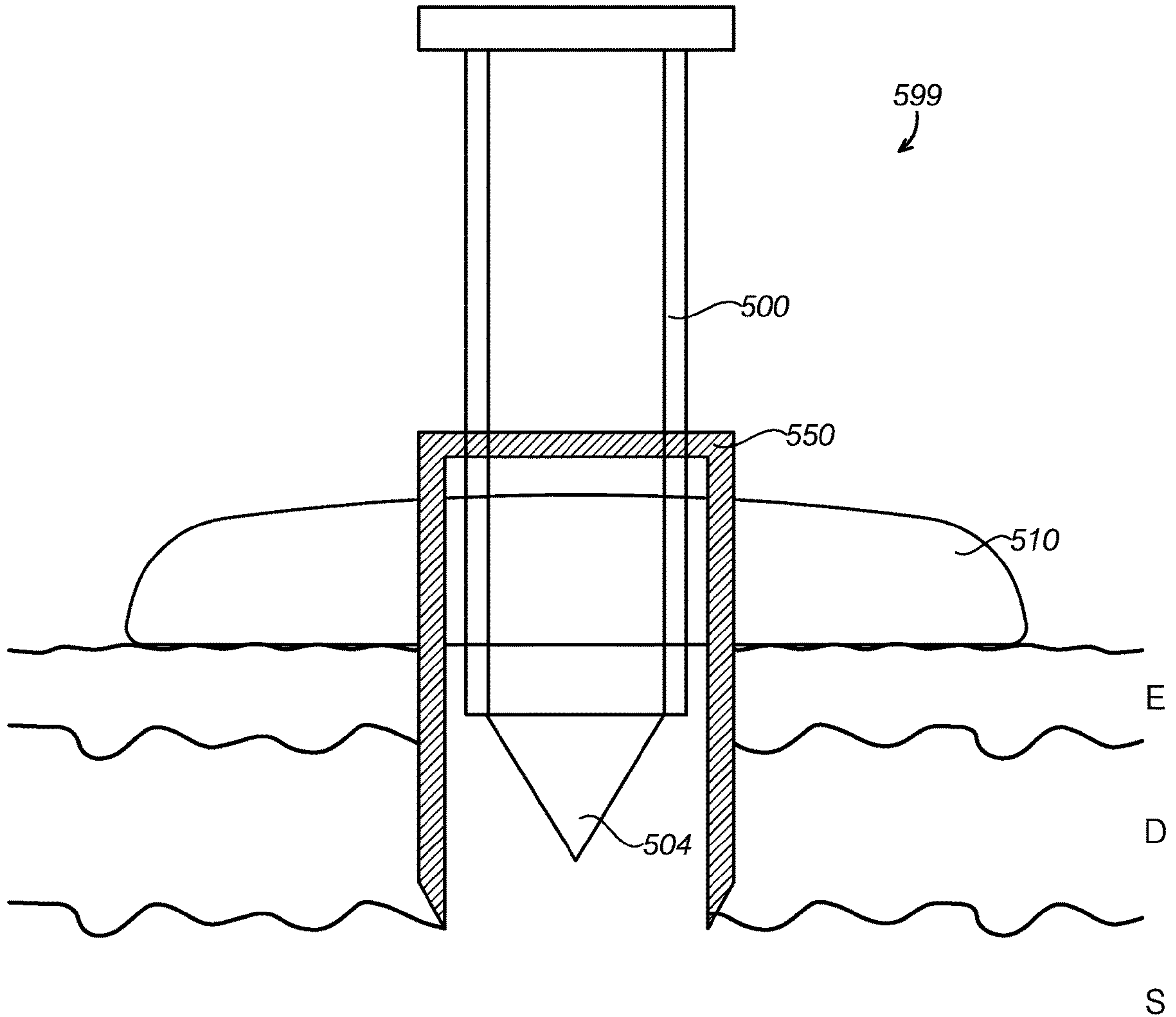
FIGS. 6A and 6B show the sequence of steps that use the outer introducer to first pierce the skin and then passage of the middle cannula and inner needle through the lumen of the outer needle into the subcutaneous tissue.
Figure 6B:
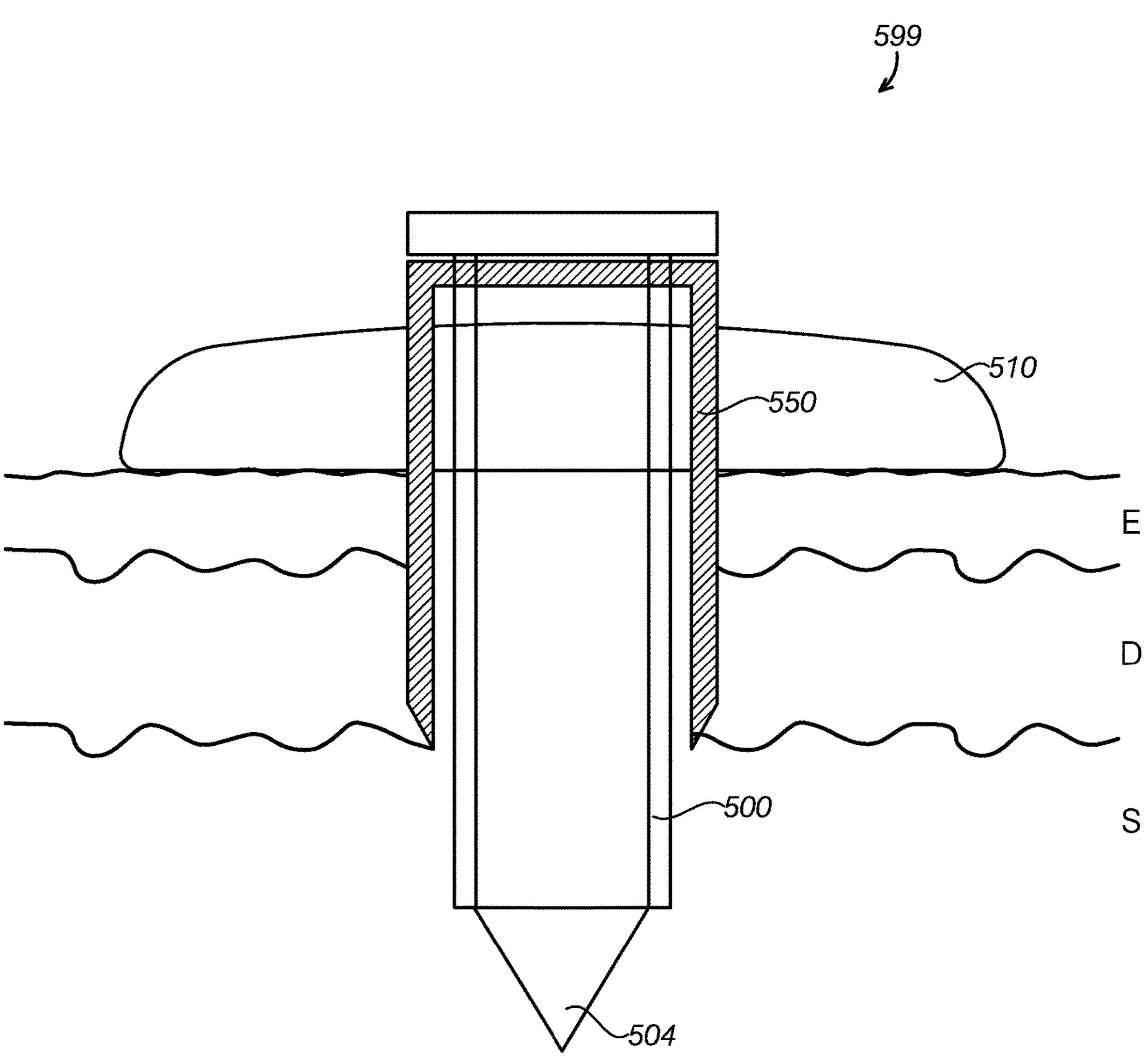

Referring to FIGS. 6A-6B, in use, the outer introducer 550 housed within the external platform 510 of the system 599 first be placed through the skin (epidermis E and dermis D) and then the needle 504 and cannula 500 can be placed through the lumen of the outer introducer 550 into the subcutaneous tissue S. As shown in FIG. 6B, the cannula 500 and inner needle 504 will extend much further into the tissue than the outer introducer 550. For example, the cannula 500 and inner needle 504 can extend 5-9 mm below the external platform 510. The inner needle 504 can then be left in the body or removed.

Referring still to FIGS. 6A-6B, the cannula 500 and inner needle 504 can be made smaller, thinner, and more flexible than commercial CSII catheters because they do not need to pierce the epidermis E and dermis D. For example, the diameter can be 25 to 32 gauge. The thickness can be 0.004" to 0.012".

In some embodiments, the method of introduction of the cannula can be automatic. The automated CSII catheter introducer can use a mechanical mechanism to perform the following sequence of actions: (1) insert the outer introducer through the epidermis and dermis to make a pathway through the skin, (2) insert the inner needle/cannula through the outer introducer's channel to a depth of 5-9 mm below the epidermis and dermis into the subcutaneous tissue, (3) retract the outer introducer back into the CSII catheter's platform, and (4) retract the inner needle out of the body, leaving the flexible cannula 5-9 mm within the subcutaneous tissue. The inner needle can remain with the automated introducer for safe disposal. In some embodiments, the outer introducer 550 extends out of the external platform 510 to pierce the skin (1.0-1.2 mm) and then retracts back into the platform 510 via a spring mechanism.

The cannula can be inserted at 90 degrees, 45 degrees, or any angle therebetween relative to the skin surface. A 90 degree angled catheter can be limited to a 6 to 9 mm length cannula to avoid insertion into skeletal muscle. A 45 degree angled catheter can have a longer length cannula 8 to 12 mm that remains within the subcutaneous adipose tissue.

Figure 7:
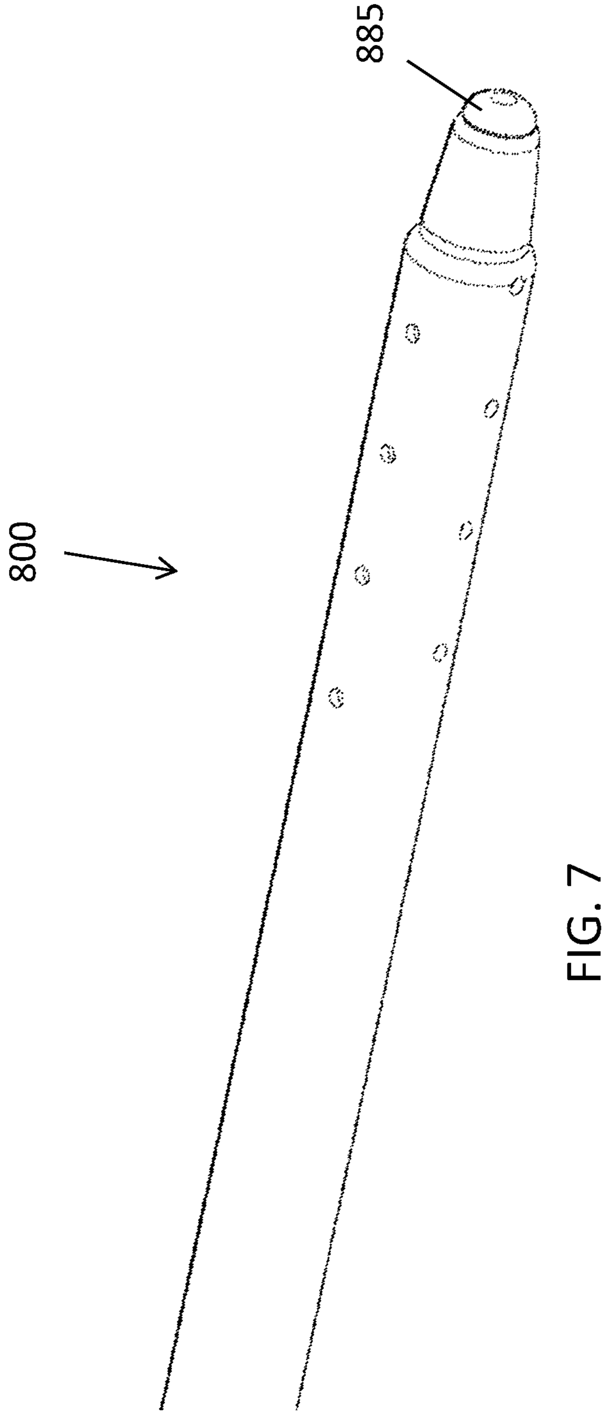
FIGS. 7-8 show a catheter with a split septum valve at the distal end of the flexible cannula.
Figure 8:
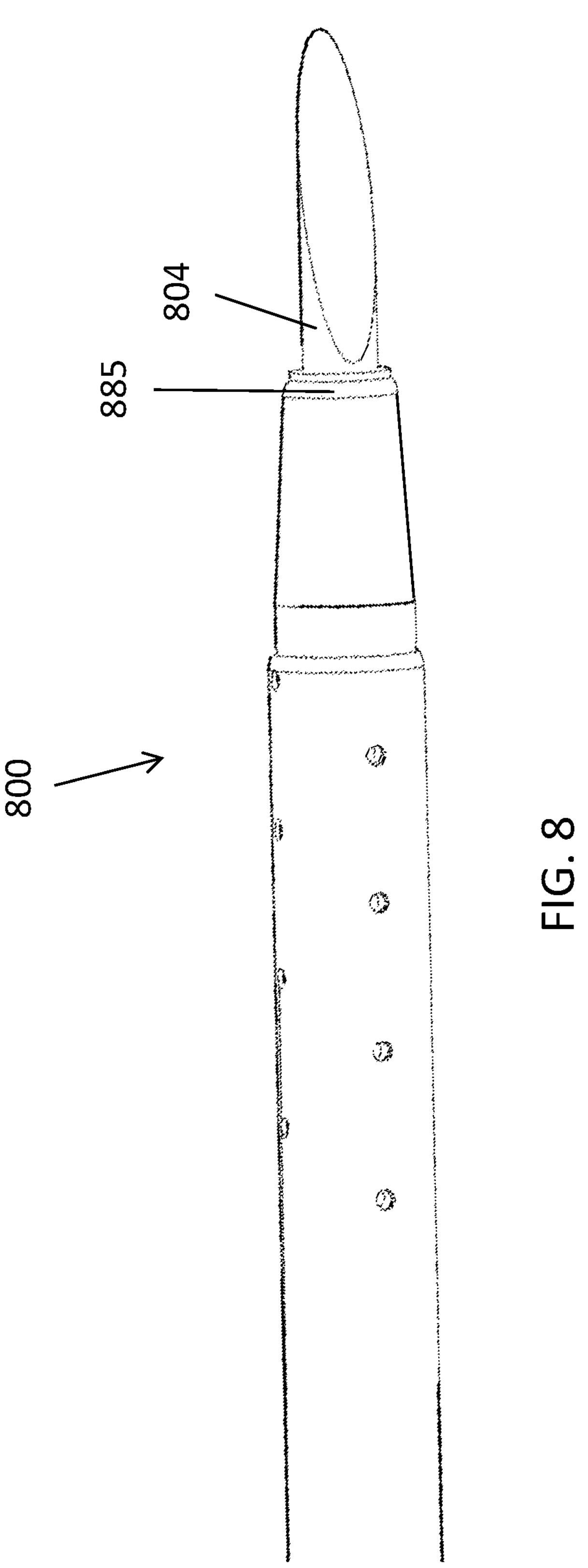

In embodiments where an inner needle is used (such as shown in FIGS. 4-6B), the distal end of the cannula can be configured to close after the inner needle is removed to ensure that insulin is provided mostly through the side holes and a little or no insulin comes out from the distal end. For example, as shown in FIGS. 7-8, the cannula 800 can include a split septum valve 885 at the distal end thereof. The split septum valve 885 can be configured to maintain a partially closed or fully closed position (as shown in FIG. 7), but open when a needle 804 is inserted therethrough (FIG. 8). The septum valve 885 can have a silastic plug affixed distally to the internal lumen of the delivery catheter. In use, the needle 804 can be inserted through the lumen of the cannula 800 and through the septum valve 885 to provide lead-in insertion. Once the cannula 800 is properly located, the needle 804 can be extracted, and the septum valve 885 can close, providing a seal to the distal tip of the cannula 800.

Figure 9:
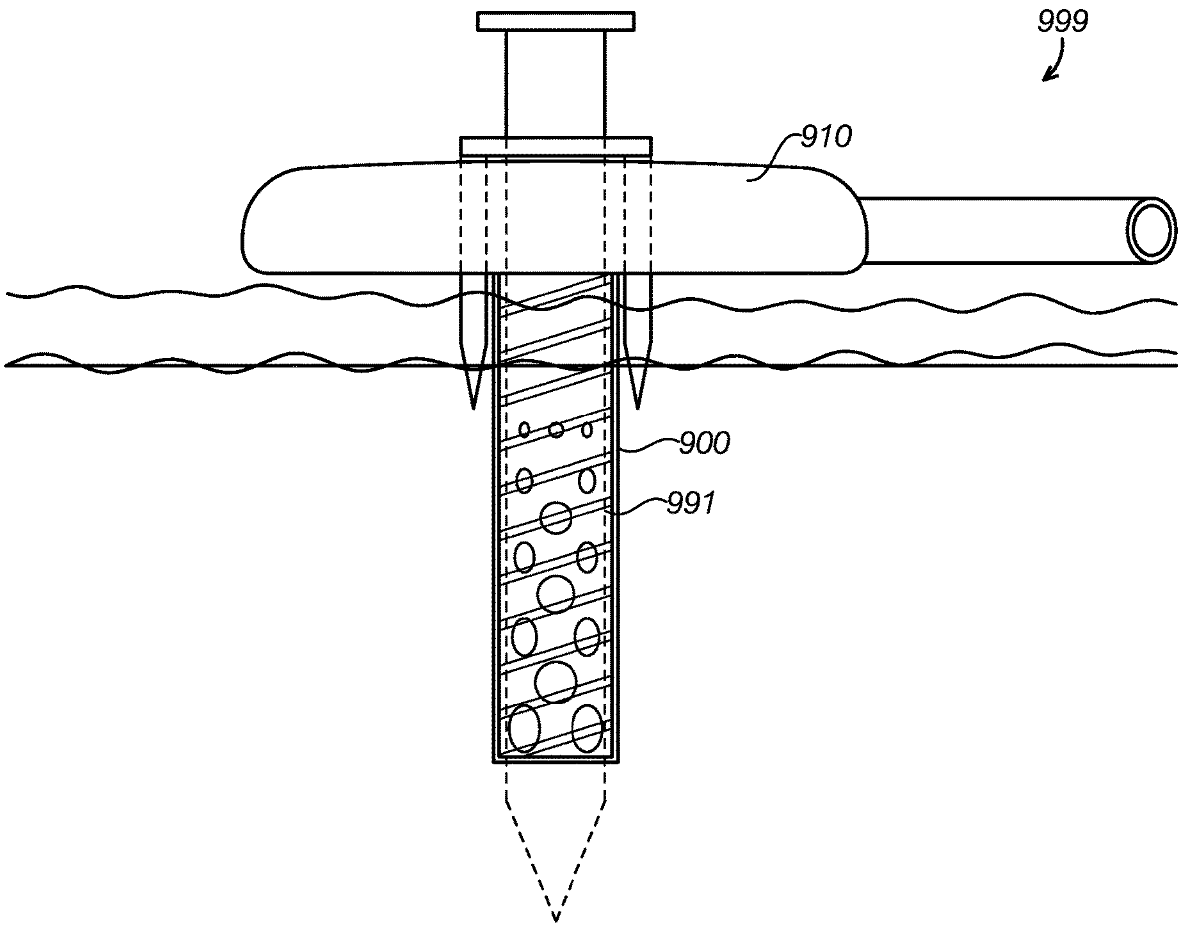
FIG. 9 shows a continuous subcutaneous infusion catheter with a filament within the wall of the flexible cannula for reinforcement and/or to heat the cannula and surrounding subcutaneous tissue.

Referring to FIG. 9, in some embodiments, the catheter system 999 can include filaments or wires 991 wound around and/or within the wall of the cannula 900 for reinforcement. The wires 991 can be, for example, Nichrome or Kanthal wire. The wires 991 can be very thin, such as 20 μm to 200 μm while the cannula can be 27-gauge or smaller with a wall thickness of 0.003" to 0.01". In some embodiments, the wires can be wound between 1 and 100, such as between 20 and 80, such as between 40 and 60 turns of the wire per millimeter of cannula. The wires 991 can be metal, polymer, carbon nanotubes, or graphene. Further, in some embodiments, the wires 991 can be braided. The wires 991 can facilitate complete/reliable insertion through the epidermis/dermis and 6 to 8 mm into the subcutaneous tissue while maintain flexibility and minimizing kinking of the cannula 900.

In some embodiments, the wires 991 can be used to heat the cannula 900 and adjacent subcutaneous tissue, such as through a connection to a battery within the external platform 910 the battery of the pump. The wires 991 can heat the cannula and/or fluid being delivered, for example, to a temperature of between 30° C. and 50° C., such as between 37° C. and 42° C. In some embodiments, heating the cannula can reduce the viscosity of the fluid near the absorption site to allow for better flow and fluid distribution through the tissue and/or better fluid absorption. Further, heating the tissue can increase local capillary blood flow and metabolism of the adjacent cells, thereby increasing the rate and precision of insulin absorption (rapid on/off insulin pharmacokinetics and pharmacodynamics) and extending the possible duration of clinical use.

A similar catheter system 1499 including a wire reinforcement 1491 is shown in FIGS. 14A-14D. Here, the wires 1491 are in a cross braid pattern along the cannula 1400 to provide uniform stiffness to the cannula in any loaded direction. In some embodiments, the braid can provide very specific directional reinforcement rather than uniform reinforcement.

In some embodiments, the wires 991 or 1491 can be a coil of insulated heater wire wrapped around a steel cannula. In other embodiments, the wires 991 or 1491 can be wrapped around an inner lumen of the cannula and coated with a second tube to create a composite catheter. In some embodiments, the wires 991 or 1491 can be injection molded using flexible wires encased within the cannula wall. In some embodiments, the wires 991 or 1491 can be produced by an over-molding method to hold the wires between the two polymer materials.

To control the temperature of the wires 991 or 1491 when used as heating elements, a temperature sensing mechanism can be used, such as a thermocouple, thermistor, or RTD. In some embodiments, a thermocouple or thermistor can be built into the body or tip of the cannula. In other embodiments, a thermocouple or thermistor can be attached to the outside of a metal cannula and/or outside of the body. In some embodiments, the temperature sensing element can be just proximal to the first hole that delivers fluid to the patient so as to precisely control the fluid temperature that reaches the body. Further, in some embodiments, the temperature sensing element can be used to confirm delivery of an insulin bolus. For example, the insulin pump temperature can be 21° C. to 23° C. while the background tissue temperature can be 28° C. to 36° C. A decrease in temperature during insulin bolus can confirm delivery of the insulin.

In some embodiments, the wires 991 or 1491 can be used to affect the transmission of mechanical vibrational energy from the cannula into the adjacent subcutaneous tissue, as described further below.

In some embodiments, an electric current can be passed through the wires 991 or 1491 (or even through the cannula if metal) to heat the local tissue enough to cause increased capillary blood flow. Further, in some embodiments, high frequency vibration (ultrasound) can heat the local tissue enough to cause increased capillary blood flow.

In some embodiments, the wires 991 or 1491 can be shaped like a continuous coil (1 to 100 coils per millimeter of cannula), helix, or vertical "fence posts". The wire diameter can range from 20 μm to 200 μm diameter. The wire can also be patterned like an arterial stent covered with an outer sleeve made of thin walled Teflon polymer. A thin polymer sleeve around the nanowire can produce a more flexible and compliant cannula while a thicker polymer sleeve can produce a less flexible and compliant cannula.

In some embodiments, the wire 991 or 1491 can be manufactured from a compound that changes shape (e.g., nintinol) following an increase in temperature, allowing the lumen diameter of the cannula to increase as the compound changes from room temperature to body temperature. In some embodiments, a shape-changing wire can be assembled into the cannula wall approximately 2 mm below the CSII catheter platform to form a mechanical "anchor". Once implanted, the wire can curve upward to anchor the proximal end of the cannula to the underside of the dermis. An alternative embodiment locates the wire "anchors" at the distal end of the cannula. Anchoring the distal end of the flexible cannula with the subcutaneous tissue may affect the transfer of vibrational power into the adjacent layer of inflammatory tissue.

In some embodiments, the wires 991 or 1491 can be encased in a very thin wall of polymer material that is highly flexible and elastic. The wound around wire advantageously facilitates use of a very soft, thin, flexible, material with a modulus similar to human subcutaneous adipose tissue.

In some embodiments, the wires 991 or 1491 can be miniature fibers such as carbon nanotubes, graphene sheets, cellulose fiber, or fiberglass can be woven to produce optimal patterns of cannula wall reinforcement. The woven fibers can prevent kinking and structural support for insertion. The fibers can be integrated within the cannula wall polymer/plastic materials. The fibers or other materials can be made into a "stent-like pattern" that produce an optimal amount of structural support for cannula insertion and an optimal amount for flexibility and kink resistance once implanted within the subcutaneous tissue.

Figure 10:
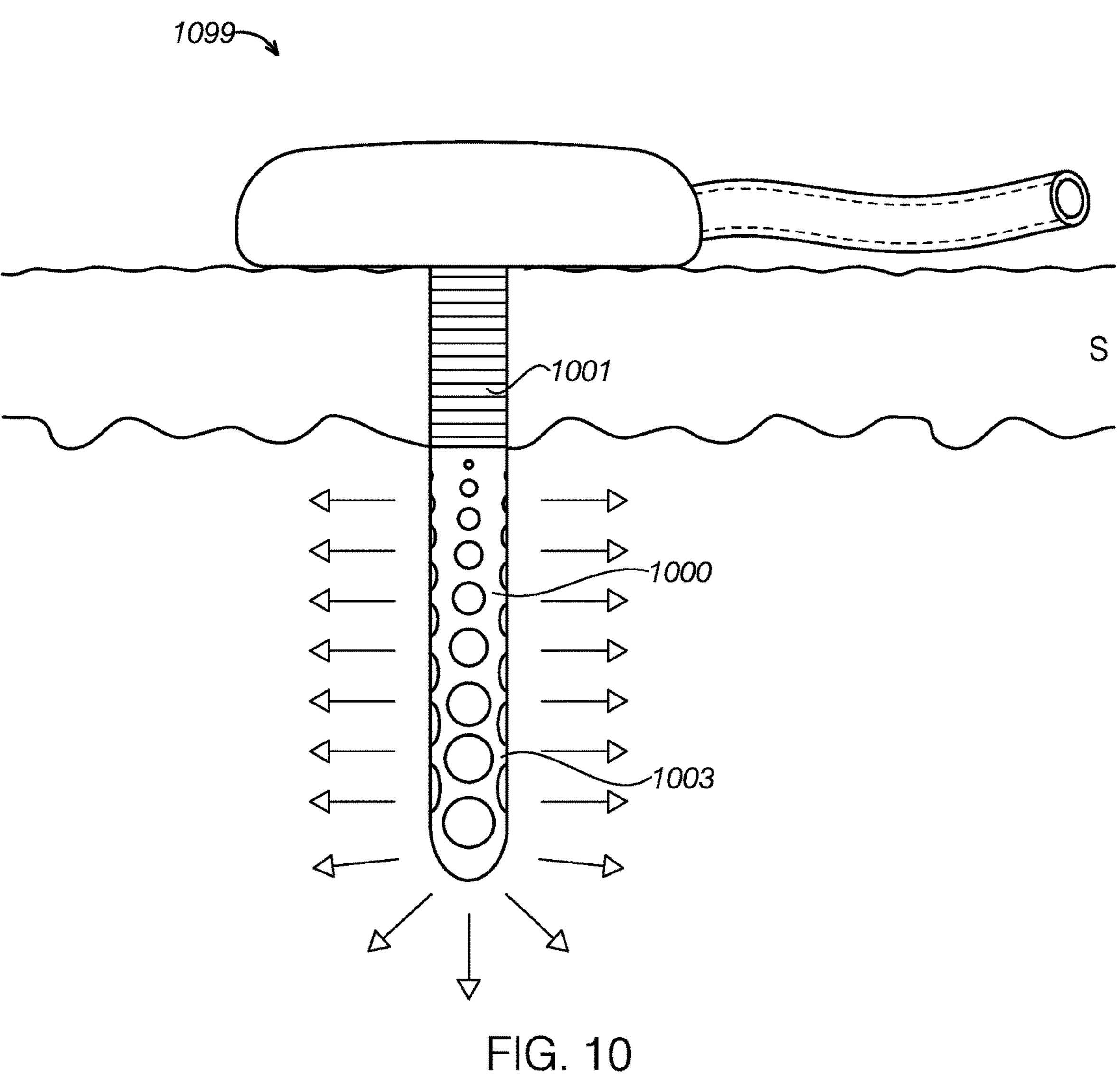
FIG. 10 shows a continuous subcutaneous infusion catheter with a highly flexible proximal cannula portion designed to minimize movement of the less flexible distal cannula portion during movement of the skin and body.

Referring to FIG. 10, in some embodiments, the catheter system 1099 can include a cannula 1000 having a distal portion 1003 with a plurality of holes 1005 and a proximal portion 1001 that is made of a more flexible material, such as highly flexible silicone. The silicone tubing can advantageously mechanically isolate the distal portion 1003 of the cannula 1000 from movement of the skin S (including epidermis and dermis) caused, for example, by body movements. Isolating the distal portion 1003 can reduce ongoing tissue damage to the capillaries and lymph vessels of the subcutaneous tissue due to body movement, leading to more precise insulin absorption over a longer period of time of use, such as 3 to 28 days in the subcutaneous tissue.

Figure 11:
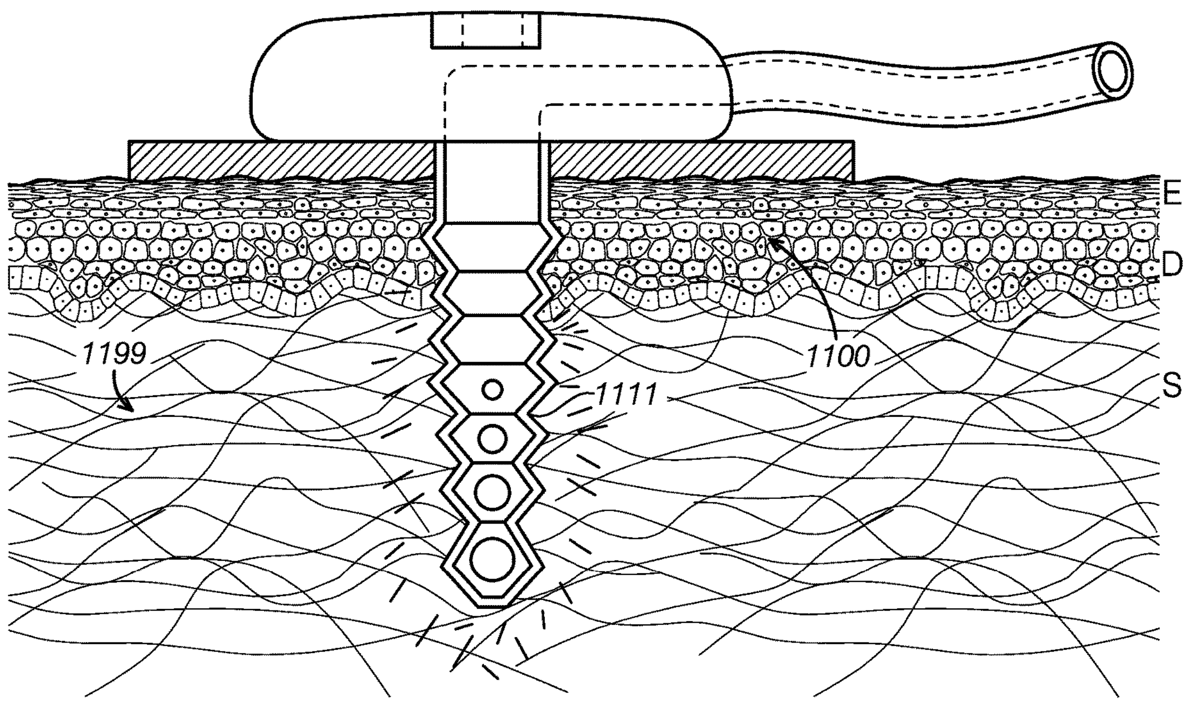
FIG. 11 shows a continuous subcutaneous infusion catheter with a flexible cannula having an outer wall that changes from smooth to an accordion-like shape after insertion within the body.

Referring to FIG. 11, in some embodiments, the catheter system 1199 can include a cannula 1100 with an accordion-style outer wall 1111. The accordion-style wall 1111 can both provide bends that help prevent the cannula 1100 from pulling out when the skin moves and provide more surface area for delivery of insulin to the subcutaneous tissue. In some embodiments, the cannula 1100 can be inserted in a long, smooth, straight configuration and then contract into the accordion shape. This movement can advantageously move the distal end of the cannula 1100 away from the area of the tissue with the most trauma (i.e., where the tip of the needle ended).

In some embodiments, wings or anchors can be added to the cannula to help keep the catheter in place in the subcutaneous tissue.

Figure 20A:
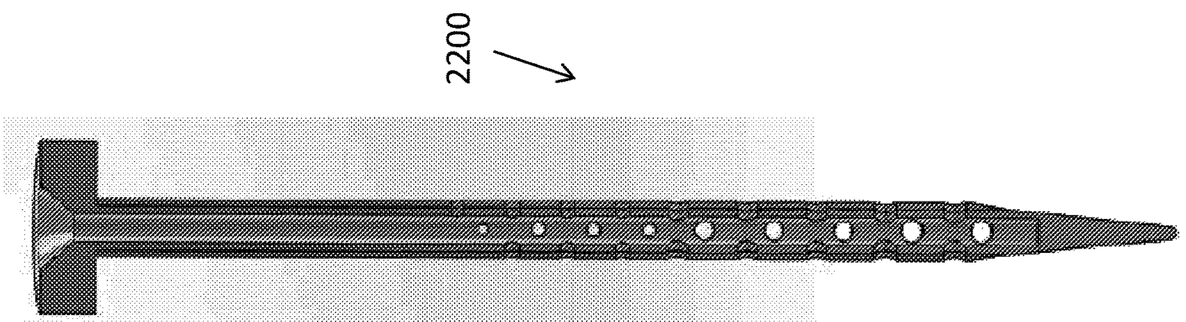
FIGS. 20A-20B show a multi-layer cannula.
Figure 20B:
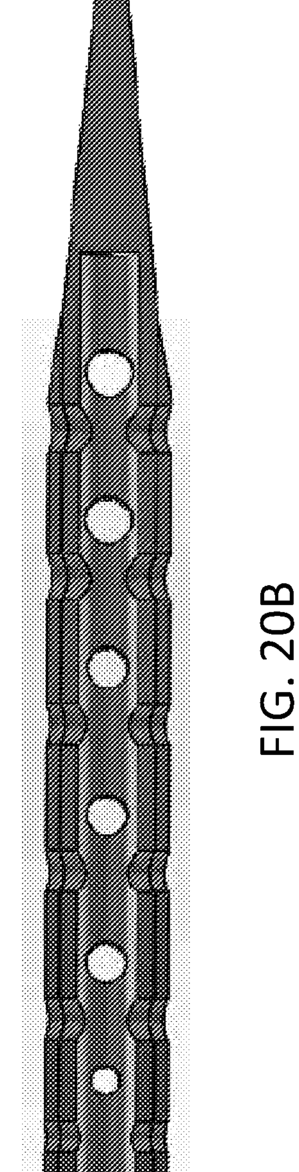

In some embodiments, the cannulas described herein can be in a multi-layer configuration, as shown in FIGS. 20A-20B. For example, in one embodiment, the cannula 2200 can include two to three layers of different polymers to provide the desired level of stiffness and lubricity. In another embodiment, the cannula 2200 can include a radially innermost polymer layer, a stainless steel braid center layer, and lubricious polymer outer layer. In some embodiments, the innermost polymer layer is rigid, and the outermost polymer layer is soft/flexible. In other embodiments, the innermost polymer layer is soft/flexible, and the outermost polymer layer is rigid. In some embodiments, the polymer materials can be stiffer at the time of cannula insertion, and highly flexible once implanted within the subcutaneous tissue (due to the increase in temperature).

Figure 21:
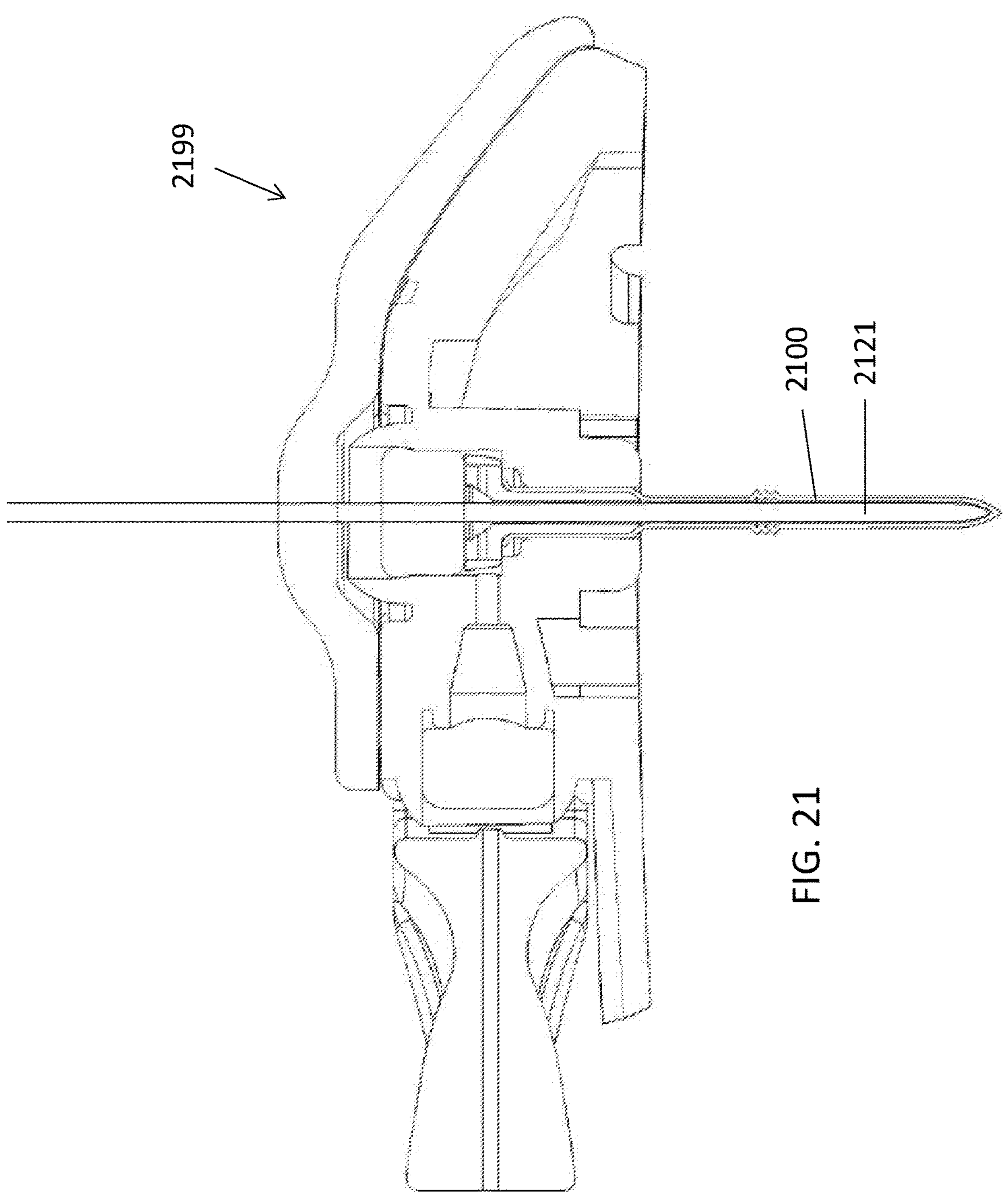
FIG. 21 shows a subcutaneous infusion catheter system with a cannula and mandrel therein.

Referring to FIG. 21, in some embodiments, a catheter system 2199 can include an outer cannula 2100 and an inner supportive mandrel 2121. The mandrel 2121 can be more rigid than the cannula 2100 and can be configured such that the cannula 2100 fits closely thereto, i.e., substantially conforms to the outer dimensions of the cannula 2100. In some embodiments, the cannula 2100 can have a completely closed end, and the mandrel 2121 can fit within the closed end. By adding the rigidity of the mandrel 2121, an inner introducer needle may not be needed (i.e., the combined mandrel 2121 and cannula 2100 can push through the skin and/or subcutaneous tissue to lodge the system in place).

Figures 24A, 24B:
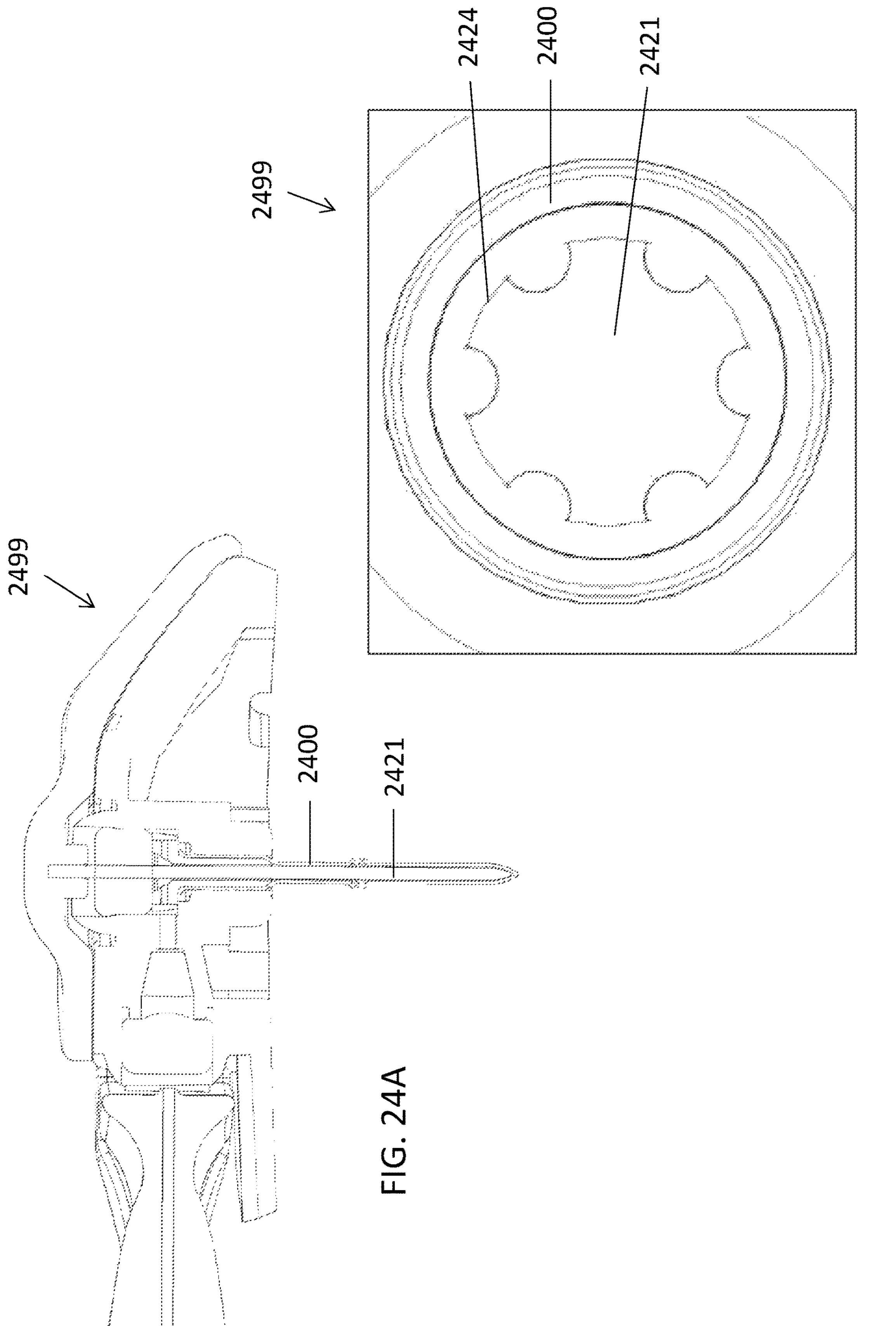
FIGS. 24A-24B show a subcutaneous infusion catheter system with a cannula and mandrel having spines therein.

Referring to FIGS. 24A and 24B, in some embodiments, such as system 2499, the mandrel 2421 can include spines 2424 extending radially therefrom. The spines 2424 can ensure that space is maintained between the mandrel 2421 and the catheter 2400. In such an embodiment, the mandrel 2424 can be permanently left inside the catheter 2400 while allowing the delivery fluid to pass in the channels formed between the spines 2424 and the inner wall of the catheter 2400.

Figure 29A:
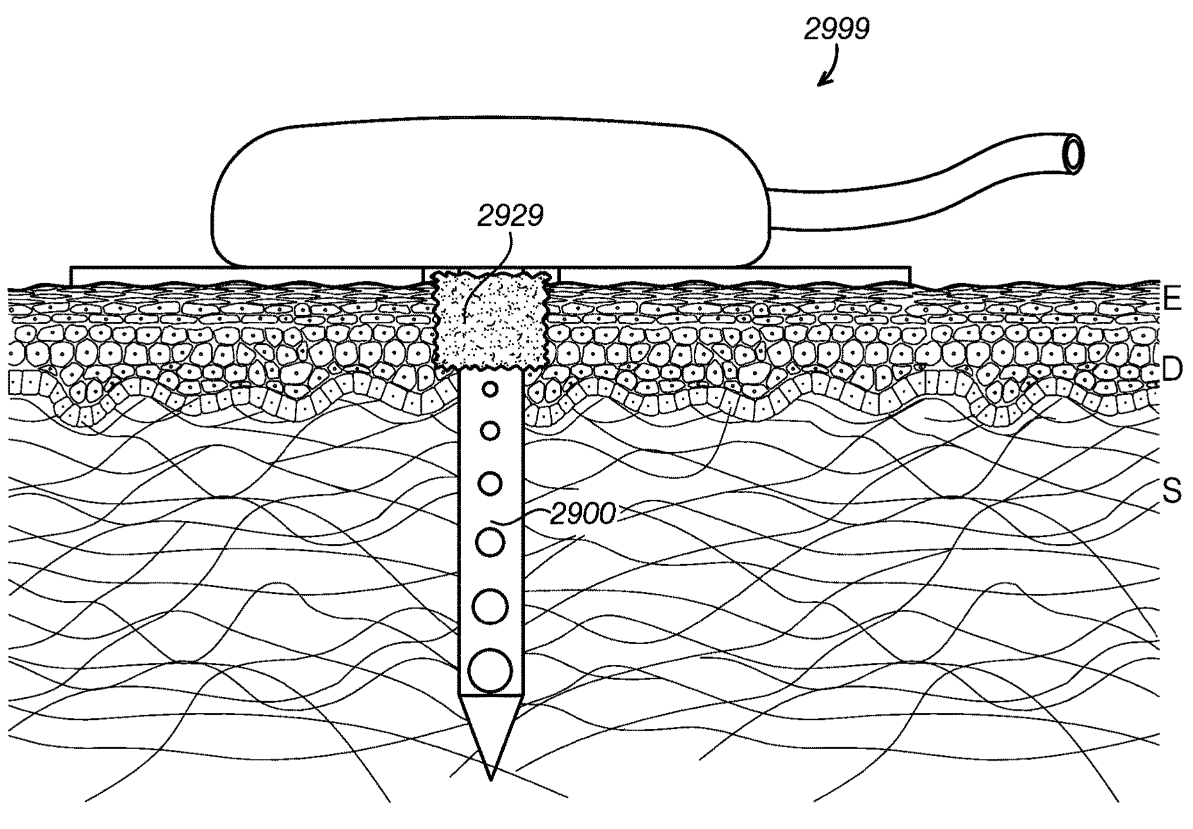
FIGS. 29A and 29B shows a subcutaneous infusion catheter system having a cannula with a porous scaffold at the proximal end.
Figure 29B:
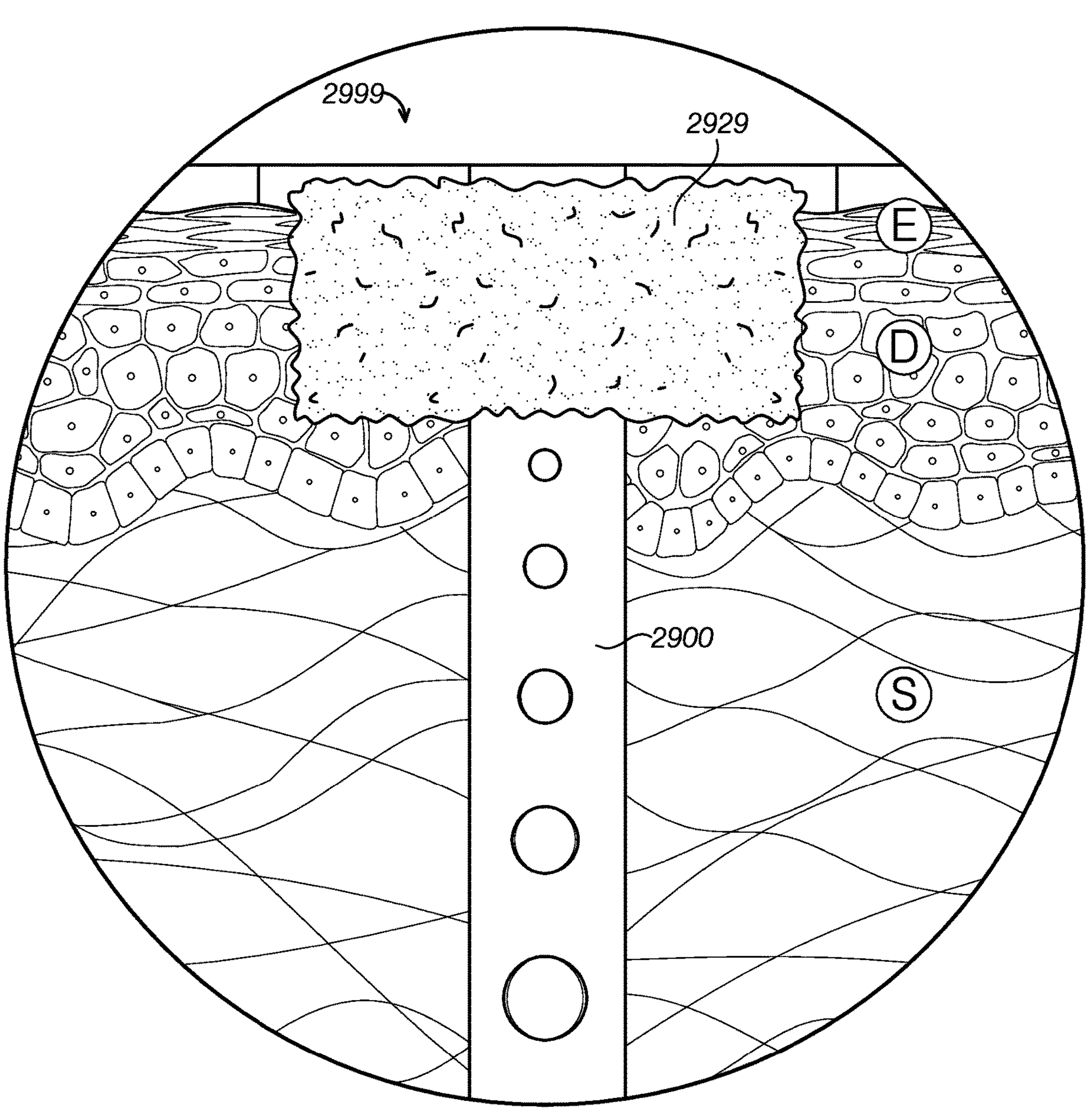

In some embodiments the proximal 1 to 2 mm of the cannula can be textured or surrounded by a thin porous membrane (e.g., Dacron or ePTFE) designed to promote the mechanical adhesion/attachment of dermis cells to the outer surface of the cannula. Dermal cells can migrate and attach to the cannula wall within hours of cannula implantation. As a result, a localized region of high flow resistance will be produced to ensure that insulin stays within the subcutaneous tissue and does not leak onto the skin surface. An exemplary such system 2999 is shown in FIGS. 29A and 29B. The catheter system 2999 can include a porous scaffold 2929 around the cannula 2900 for better integration with the epidermis and dermis. Thus, as shown in FIGS. 29A and 29B, the cannula 2900 can be implanted within the subcutaneous tissue S and the scaffold 2929 can be positioned within the epidermis E and dermis D. The scaffold 2929 can be made of a biomaterial (e.g., Dacron, ePTFE, etc.) that facilitates the mechanical attachment and ingrowth of adjacent epidermis and dermis tissue. The scaffold 2929 can be 5 micrometers-1,000 micrometers, such as 10 micrometers to 100 micrometers thick. In some embodiments, the scaffold width can extend slightly above the epidermis E and slightly below the dermis D to optimize surface area of skin attachment. In some embodiments, the scaffold 2929 can be covered by a bactericidal material that helps prevent the travel of bacteria into the incision. Further, in some embodiments, the scaffold 2929 can be coated with a material that promotes surface attachment, such as fibronectin, hyaluronase, collagen, elastin, RGD peptides, and/or artificial basement membrane.

Figure 30:
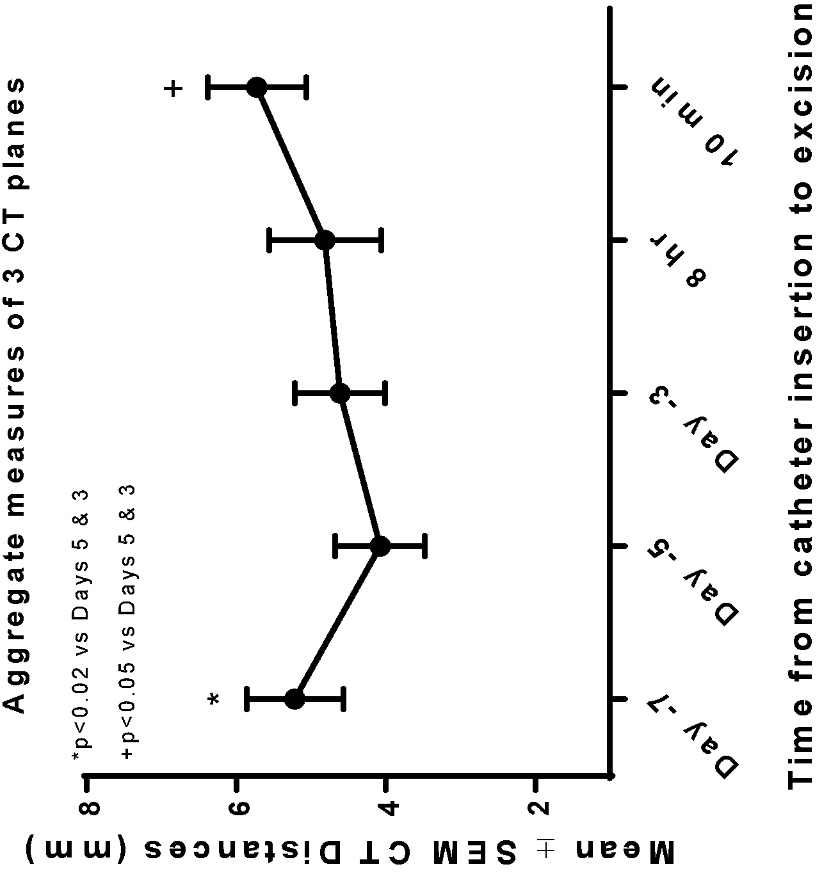
FIG. 30 shows a graph of distribution of fluid relative to the time from catheter insertion.

Thus, referring still to FIGS. 29A and 29B and 30, the tissue can grow into the scaffold 2929 to form a mechanical seal from the external environment within 4 to 12 hours of implantation. The epidermis E and dermis D attach to the scaffold to form a mechanical barrier against the downward spread of infection and to prevent insulin from flowing onto the skin S surface. The scaffold 2929 advantageously helps increase the precision of insulin absorption for a longer implantation time with a lower risk for infection. In one embodiment, the cannula 2900 can be easily removed from the scaffold 2929 such that the scaffold 2929 can be left in the body after use to enhance wound healing without scar formation. Further, in some embodiments, the scaffold 2929 can be biodegradable.

In some embodiments, the infusion catheter systems described herein can have a mechanism that mechanically vibrates the cannula and adjacent subcutaneous tissue. The cannula can be vibrated in a continuous or intermittent fashion such that the damaged tissue surrounding the cannula (containing thrombus, tissue debris, edema fluid, and inflammatory cells) is loosened or broken into pieces. Vibration of the thrombus and inflammatory tissue may increase the rate of insulin movement from the CSII catheter's cannula to the adjacent capillaries and lymph vessels. In some embodiments, vibration may further be used to provide confirmation to the user that an insulin bolus delivery has occurred.

Figure 32:
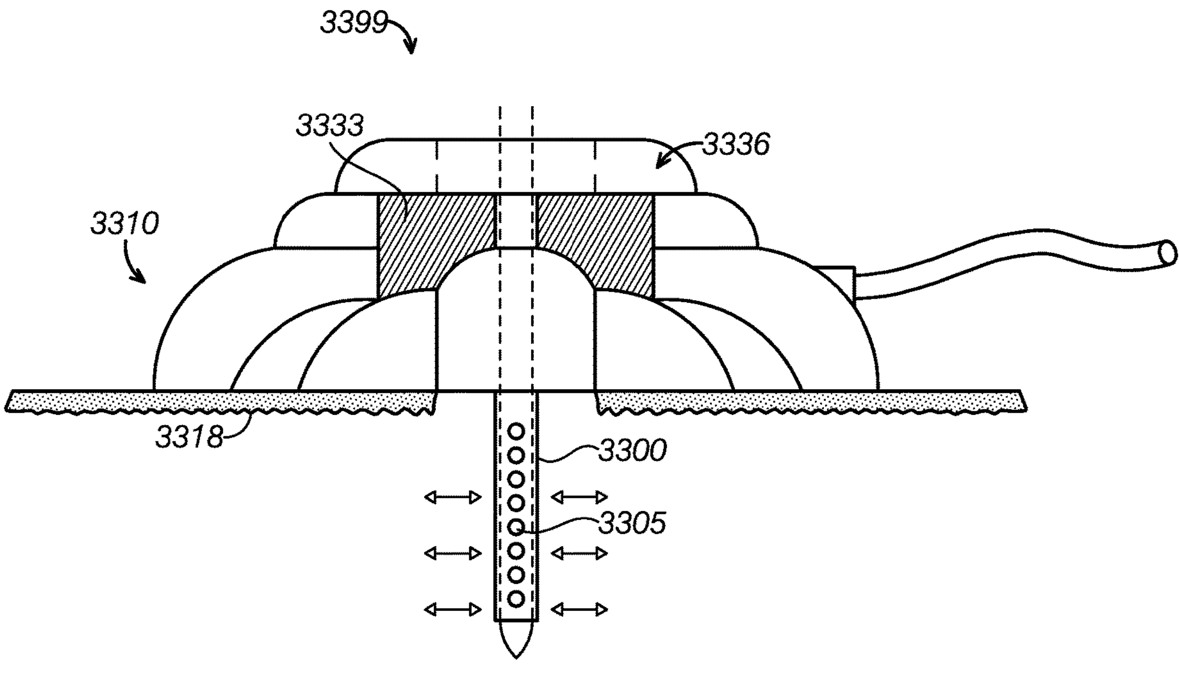
FIG. 32 shows a subcutaneous continuous infusion catheter with a cannula that is configured to vibrate.

An exemplary infusion catheter system 3399 including vibration is shown in FIG. 32. This embodiment of the CSII catheter has a flexible cannula 3300 with multiple holes 3305 of the same or different diameter, as described herein. The external platform 3310 contains a disc-shaped vibration motor 3333 that vibrates and a battery 3336 to power the motor 3333. The vibration motor 3333 is mechanically coupled to the proximal end of the cannula 3300. When the cannula 3300 vibrates within the subcutaneous tissue, the frequency of vibration can produce low frequency macroscopic movement. Further, the amplitude of vibration can be low, medium, high, or variable. The duration of vibration can be short, medium, long, or continuous and can be linear or oscillatory.

In some embodiments, the patient can activate a switch or button to turn the vibration mechanism on and off around the time of a meal bolus. In other embodiments, a controller can be configured to vibrate the cannula 3300 based on data from a sensor (e.g., pressure sensor, flow sensor, or temperature sensor) to indicate that fluid is being delivered. In other embodiments, a timer can activate the vibration at a set time (e.g., every 15 minutes).

Referring still to FIG. 32, the adhesive patch 3318 can be configured to secure the platform 3310 firmly to the surface of the skin for many days even during vibration of the cannula 3300. The platform design and the adhesive design fix the platform to the skin firmly, limiting cannula movement during body movement. Less cannula movement will decrease the amount of subcutaneous tissue damage, inflammation, and fibrous tissue deposition.

In some embodiments, the infusion system can be designed so as to vibrate substantially only the cannula while keeping the rest of the system substantially still. Thus, the infusion system can include a platform, for example, that is vibrationally separated from the cannula. Keeping the cannula vibrationally separated from the rest of the catheter (e.g., the portions that attach to the skin, the sensors, the batteries, electronics, etc.) can advantageously improve patient comfort and/or reduce the size of the required vibrator and/or battery.

Figure 33A:
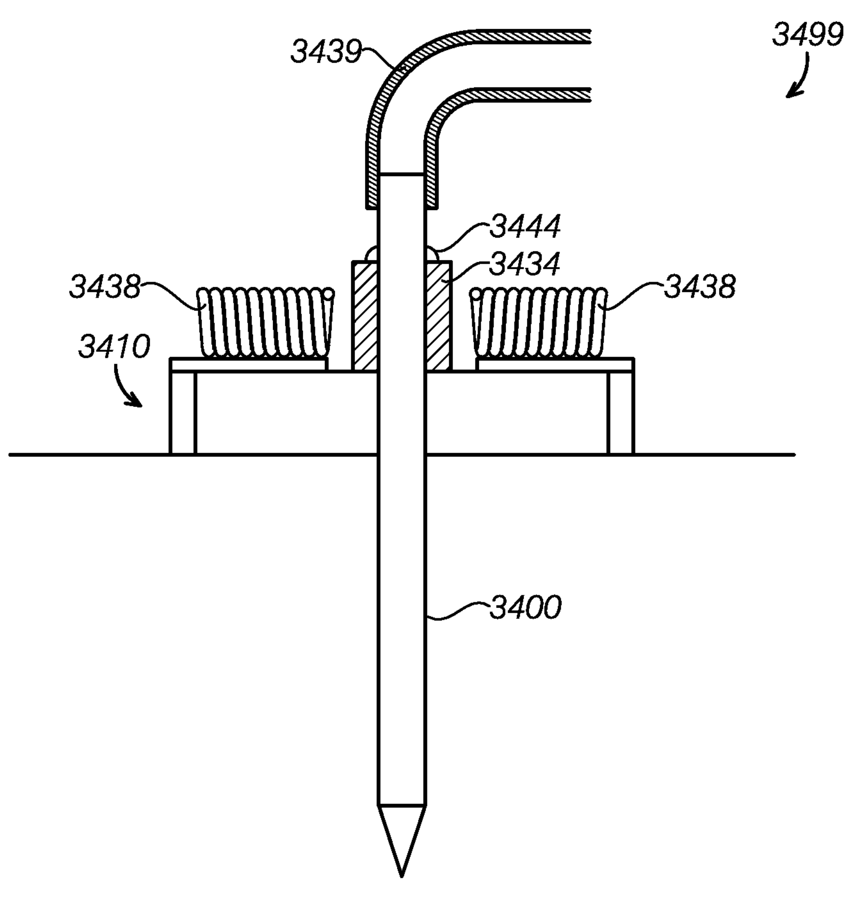
FIGS. 33A and 33B show another embodiment of a subcutaneous continuous infusion catheter with a cannula that is configured to vibrate.
Figure 33B:
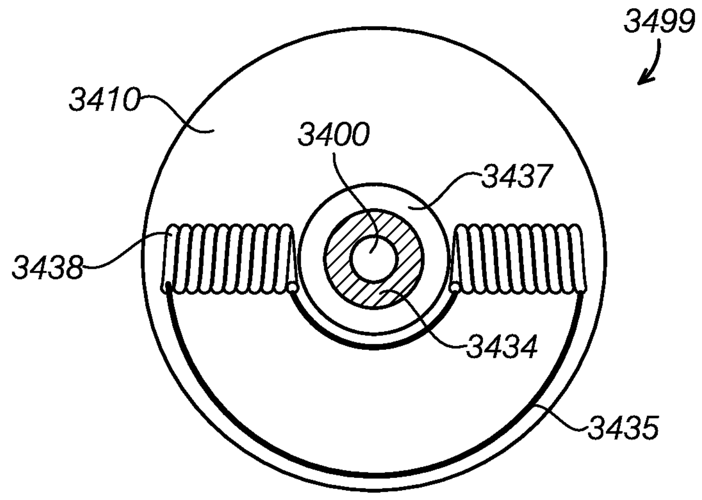

An exemplary catheter system 3499 designed to vibrate only the cannula is shown in FIGS. 33A-33B. The system 3499 includes one or more magnets 3434, such as tube magnets, bonded around the cannula 3400 with an adhesive 3444. Electric coils 3438 (connected by wires 3435) can be connected between the magnets 3434 and the external platform 3410 (e.g., which can include the adhesive for attachment to the patient, the battery, the motor, sensors, electronics, etc.) to provide the necessary current. When activated, the flow of current in one direction can move the cannula 3400 one way while the reverse flow of current can move the cannula 3400 the opposite way. A space 3437 between the platform 3310 and the magnets 3434 can provide clearance for vibrational movement of the cannula 3400 such that the platform 3410 does not move. Further, tubing 3439, such as silicon tubing, can be used to support the magnets 3434 while still providing freedom of movement. In some embodiments, two magnets 3434 that are diametrically magnetized can be used to pull and push from two sides. In some embodiments, additional magnets can be provided to increase the number of axes of vibration.

Figure 34A:
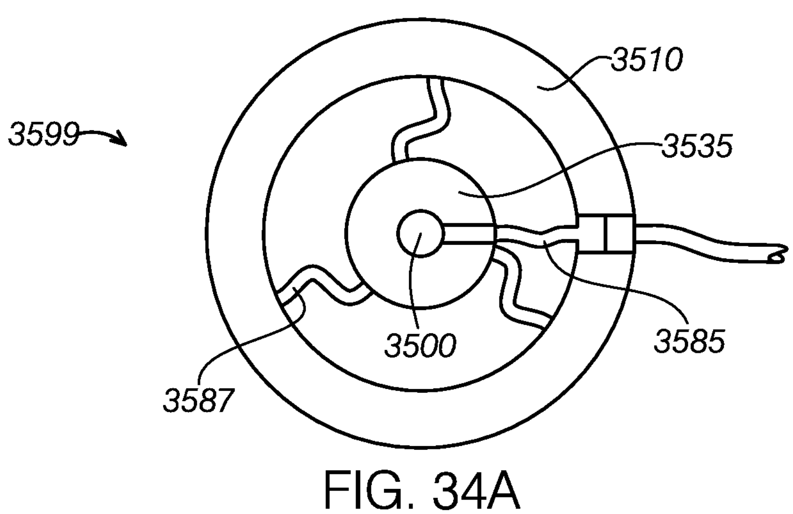
FIGS. 34A-34C show another embodiment of a subcutaneous continuous infusion catheter with a cannula that is configured to vibrate.
Figure 34B:
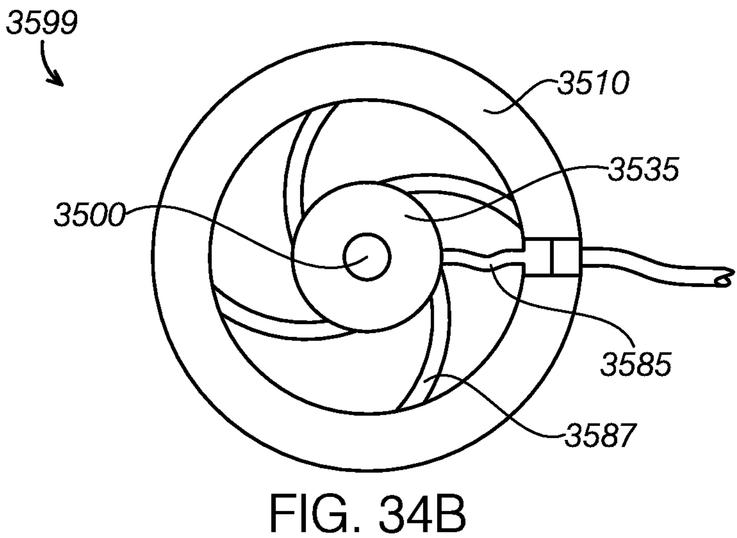
Figure 34C:
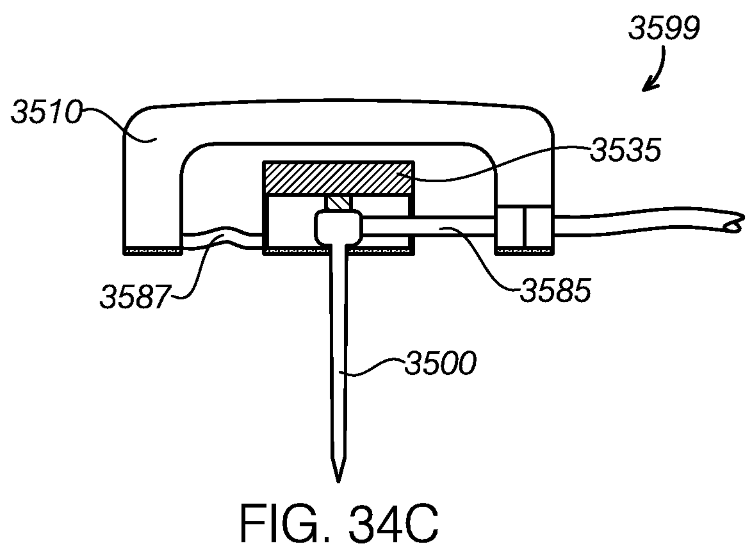
Figure 35A:
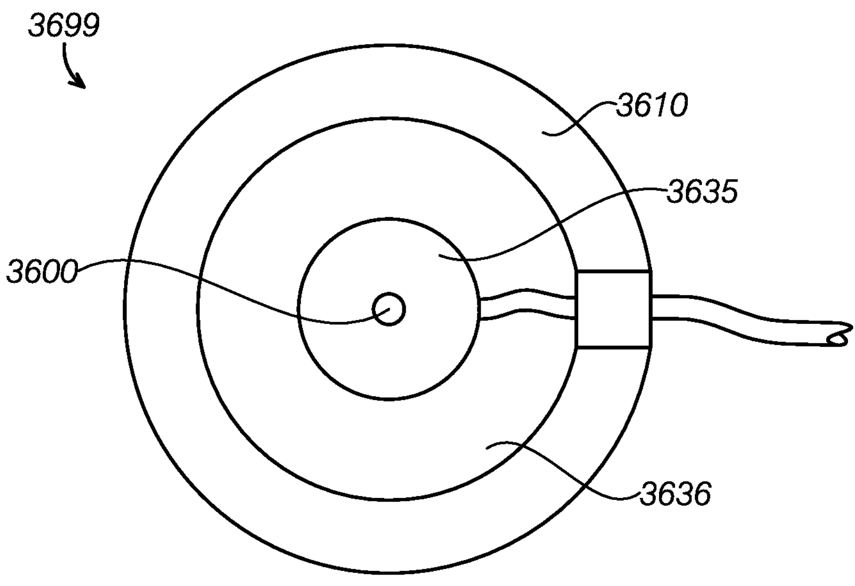
FIGS. 35A-35B show another embodiment of a subcutaneous continuous infusion catheter with a cannula that is configured to vibrate.
Figure 35B:
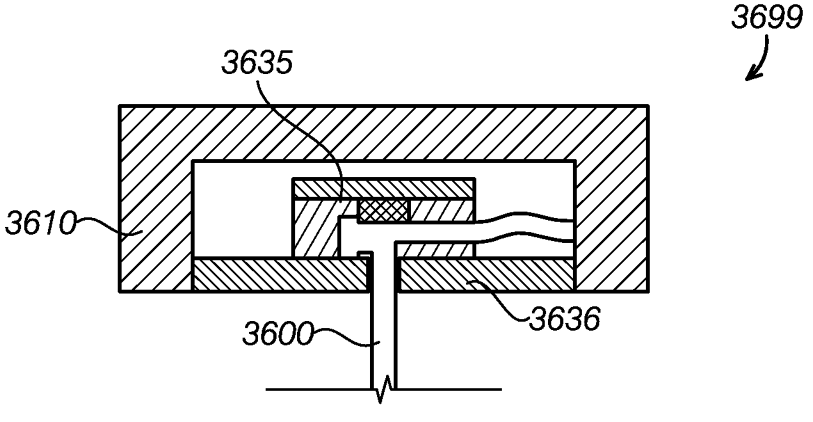

FIGS. 34A-34C show another embodiment of an infusion system 3599 configured so as to vibrate only the cannula while keeping the rest of the system still. The system 3599 thus includes an external platform 3510 (e.g., which can include the adhesive for attachment to the patient) separated from a cannula port 3535 (which can include the vibration motor, battery, and electronics) that is configured to attach to the cannula 3500. A flexible member or link 3587, such as a flexible arm, can be used to connect to the platform 3510 to the cannula port 3535. A flexible connection 3585, such as flexible tubing, can be used to provide delivery fluid from the reservoir. Thus, in use, the cannula 3500 can be vibrated by the motor in the port 3435 without vibrating the platform 3510 and associated adhesive, thereby ensuring that strong adhesion is maintained. FIGS. 35A-35B show a similar system 3699 in which the external platform 3610 is separated from the cannula port 3635 and cannula 3600 by a flexible disc membrane 3636. The flexible disc membrane 3636 can be made, for example, of silicone or neoprene. In some embodiments, the battery, sensors, and/or electronics can be part of the platform rather than part cannula port. In some embodiments, the cannula can be mechanically isolated from the platform even when no vibration motor is used so that the cannula moves with the surrounding subcutaneous tissue during body movement and does not cause additional tissue damage over time.

The vibration described herein can include up/down, rotational, orbital, and/or side-to-side motion. Further, the vibration can be continuous or intermittent. The frequency of vibration can be selected to provide maximum clinical effect and/or minimal energy consumption. Moreover, in some embodiments, the infusion system can be configured to vibrate the cannula only when fluid is being delivered therethrough (i.e., using data gathered by one or more sensors configured to measure flow rate). In some embodiments, the infusion system can be configured to vibrate the cannula when reduced flow is detected. In some embodiments, the infusion system can be configured to vibrate the cannula when reduced effectivity of the fluid being delivered (i.e., insulin) is detected. In some embodiments, the cannula can be vibrated for 10 to 30 minutes before an insulin bolus and/or for 10 to 90 minutes after an insulin bolus to break up the layer of inflammatory tissue and heat the local tissue to increase cell metabolism and capillary blood flow.

The vibration motor for any of the embodiments with vibration described herein can be, for example, a piezoelectric element, a coin-cell vibrator, a linear-resonant-actuator, a voice coil type actuator, a brushless vibration motor, or a brushed vibration motor. In some embodiments, the vibration mechanism can include a plurality of rigid or semi-rigid strips extending along opposite sides of the cannula from the proximal end to the distal end that activate by pulling one strip and pushing on another, causing distortion of the cannula and resulting vibration when repeated at a high frequency.

Further, the mechanical energy of the vibration mechanism can be adjusted over a wide range of power (0.5 to 1,000 milliwatts), intensity (0.5 to 1,000 milliwats/cm$^2$), distance tissue moves (0.001 to 3 um), frequency (1 Hertz to 5 Megahertz), and direction (3 dimensional-up/down/left/right/in/out) to optimize cannula vibration within the subcutaneous tissue. The cannula can be vibrated continuously or pulsed on and off. Pulsing the intensity of vibration during a meal insulin bolus can increase the power delivered to the layer of inflammatory tissue without causing excess heat build-up. The cannula can be pulsed on/off (duty cycle) 1 to 1,000 times per minute at the desired vibration frequency (1 Hz to 5 MHz). The cannula can be continuously or intermittently vibrated and pulsed throughout the 7 days of implantation according to a fixed time sequence, a variable time sequence, or before, during, and after a meal insulin bolus).

Any of the cannulas described herein can be made of polymer plastic (e.g., Teflon, polyurethane, silicone, polyimide, etc.), metal (e.g., stainless steel, titanium, etc.), and/or ceramic. In some embodiments, the cannula can be semi-rigid. In some embodiments, the cannula (e.g., a semi-rigid cannula) can be manufactured either by extruding the correct diameter tubing or by molding.

In some embodiments, the infusion systems described herein can include one or more sensors configured to measure a flow rate, pressure, and/or temperature of fluid through the flexible cannula.

Although primarily described herein as being connected to an infusion set, the cannulas described herein can also be used with an insulin patch (e.g., such that the pump sits right on the skin). In such an embodiments, the reservoir may be reloadable and/or replaceable to allow the patch and cannula to be used for an extended period of time.

Further, in some embodiments, the outer surface of the cannula can be coated with one or more compounds that prevents thrombus formation (e.g., heparin, low molecular weight heparin, or platelet inhibitors), dissolves thrombus (e.g., fibrinolytic drugs streptokinase, urokinase, or tissue plasminogen activatory), prevents an acute immune response (e.g., local anesthetics such as lidocaine, mepivicaine, and bupivacaine, non-steroidal anti-inflammatory agents such as tramadol, ibuprophine, and aspirin, or glucocordicoids such as cortisol, dexamethasone), dilates arterioles to increase capillary blood flow (e.g., hydralazine, nitropruside, or nicardipine), and/or increases flow into the capillaries and lymph vessels (e.g., histamine or hypertonic saline). In some embodiments, the cannula can be coated with growth factors that increase the formation of new capillaries and lymph vessels adjacent to the cannula. The coating can be coated directly on the outside of the cannula surface or located within a porous membrane on the outside of the cannula surface that contains vesicles that dissolve over time, releasing compounds from the coating into the surrounding tissue at a specific time (i.e., controlled release). In some embodiments, mechanical vibration of the cannula and the actions of compounds that dissolve thrombus and minimize the acute immune response can work synergistically to increase the rate and precision of insulin absorption over a 1-30 day, such as 3 to 28 day period of time.

In some embodiments the most proximal holes in the cannula may be laser drilled to produce an insulin flow that is angled downward, away for the under surface of the dermal layer, to minimize the risk for insulin leakage onto the skin surface. Further, in some embodiments, the distal holes can be angled downward to maximize insulin spread into deeper subcutaneous tissue below the tip of the cannula.

In some embodiments, the infusion catheters described herein can be used to deliver insulin. Insulin can flow from the insulin pump reservoir through the flexible tubing, the platform, and the cannula into the subcutaneous tissue. That is, insulin molecules can be pushed into the tissue surrounding the cannula when the hydrostatic pressure within the cannula lumen is greater than the hydrostatic pressure within subcutaneous tissue adjacent to the cannula. Orifice number, size, and location will affect the distribution of insulin molecules into the adjacent vascular tissue. The orifice parameters are optimized to deliver insulin into a large area of vascular tissue for 7 to 14 days. Insulin can be distributed around the outside of the cannula in a "cylinder" pattern (i.e. 360 degrees around and 4-12, e.g. 5 mm, in length). A large surface area increases the rate and precision of insulin absorption from the subcutaneous tissue into the bloodstream (i.e. process rapid on-off insulin PK). Advantageously, insulin absorption PK curves for the infusion systems described herein are very similar from dose to dose and day to day for 7 to 14 days. An infusion system that produces less variable insulin PK advantageously leads to better blood glucose control.

Because the catheters described herein cause less tissue damage and distribute fluid more evenly to the subcutaneous tissue, they can be used to deliver insulin for a longer period of time than current CSII needles, such as 3 to 28 days.

Experimental Results

Exemplary fluid/insulin distribution using the insulin catheters described herein are shown in FIGS. 15A-19B.

Figure 15B:
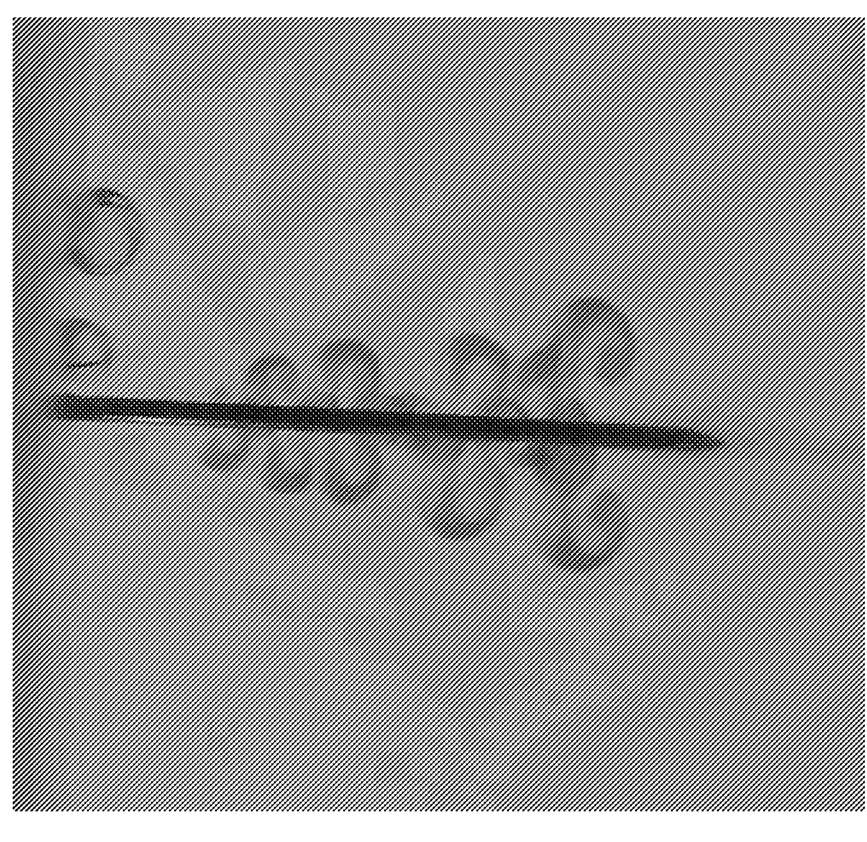
FIGS. 15A-15B show a pattern of fluid delivered from a cannula having holes sizes increasing from the proximal end to the distal end from 0.0005 mm to 0.002".
Figure 15A:
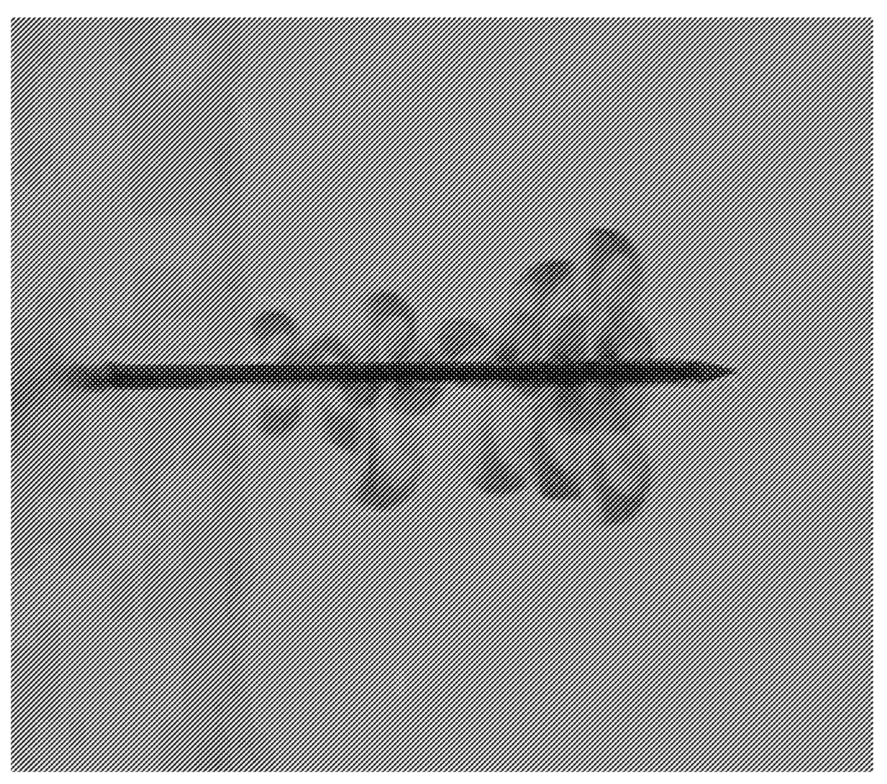
Figure 16B:
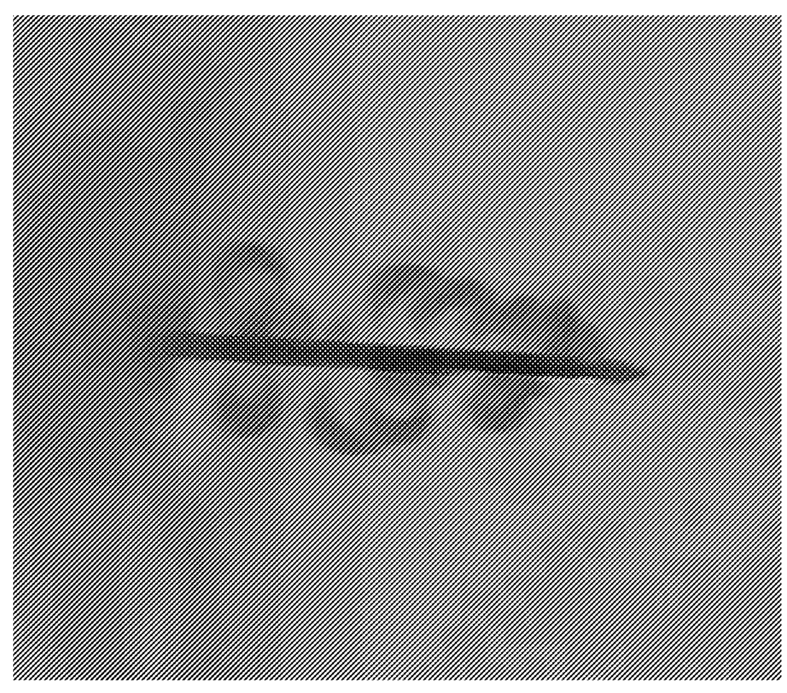
FIGS. 16A-16B show a pattern of fluid delivered from a cannula (having constant holes size of approximately 0.00095")
Figure 16A:
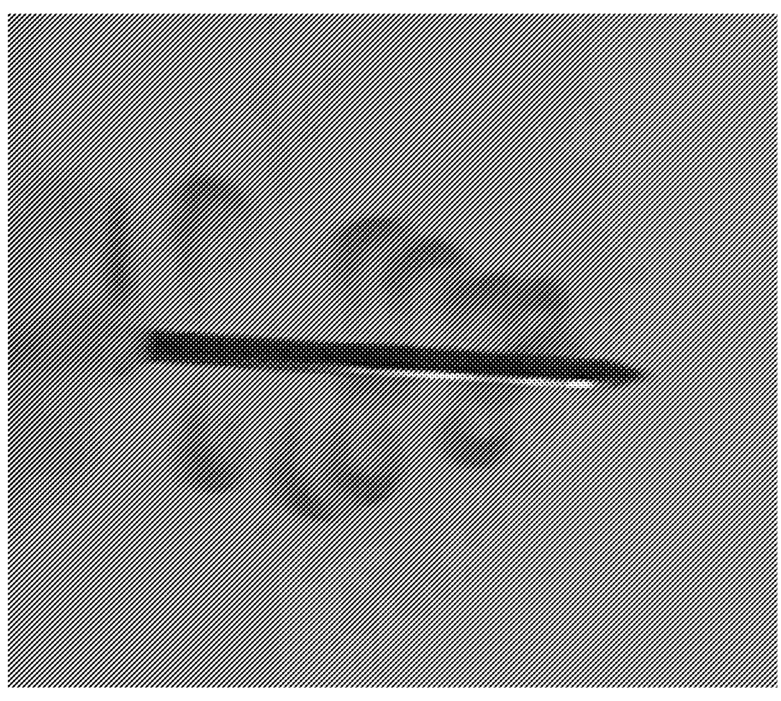
Figure 17C:
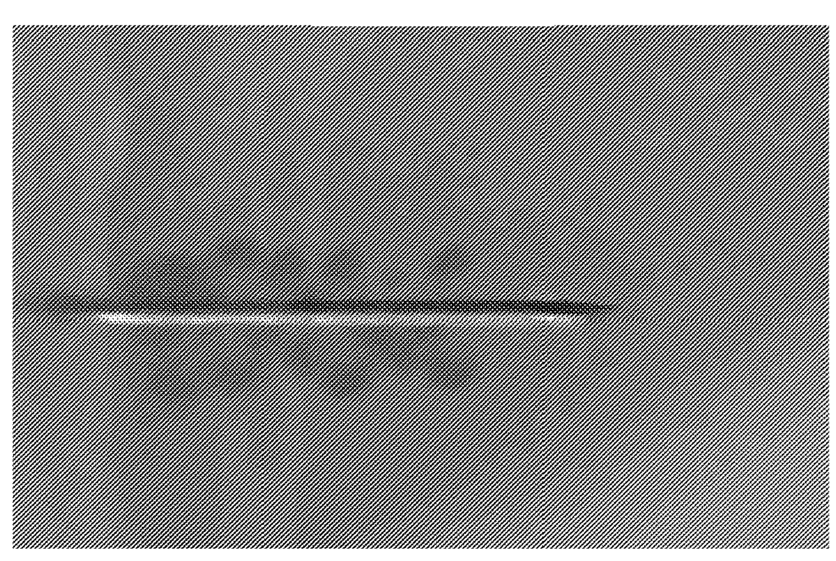
FIGS. 17A-17C show a pattern of fluid delivered from a cannula (having constant hole size of approximately 0.00075")
Figure 17B:
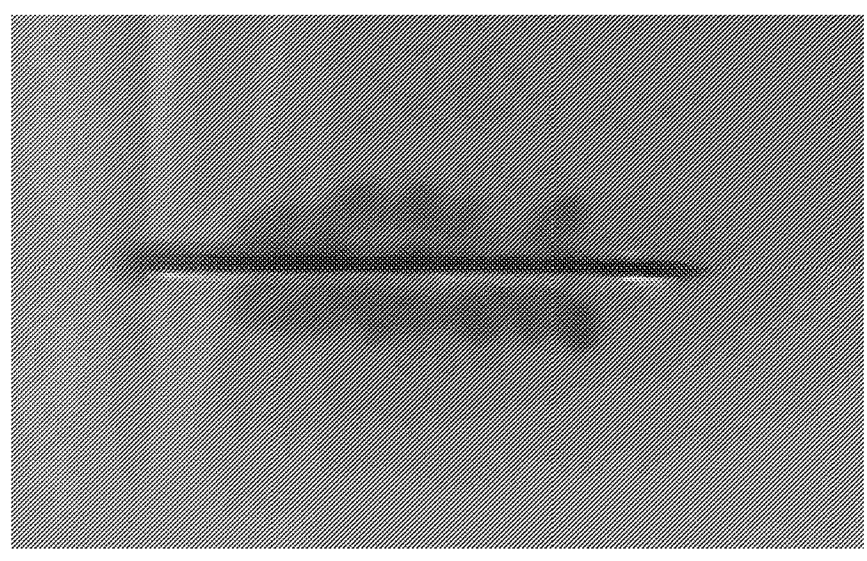
Figure 17A:
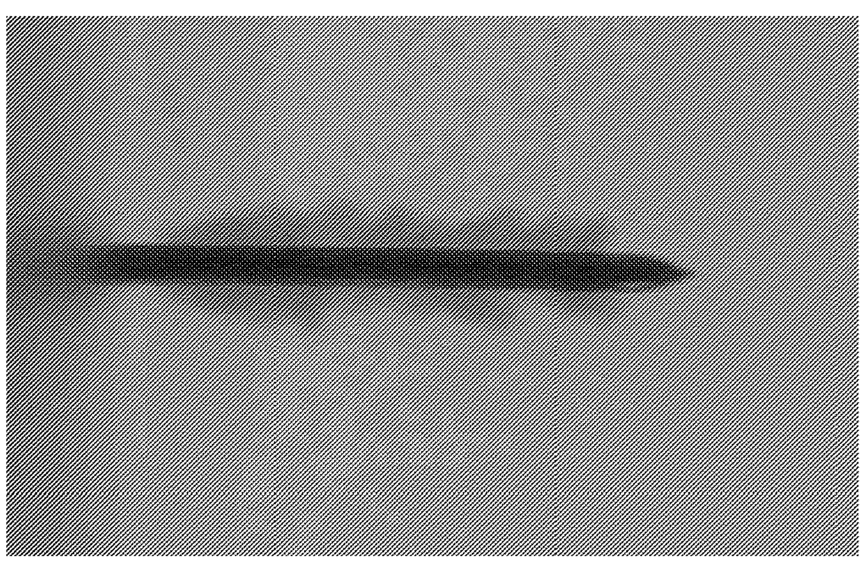

FIGS. 15A-17C show the fluid pattern produced when dye is infused through various multi orifice cannulas into water using an insulin pump. Infusing dye into water provides an objective measurement of the CSII catheter's flow characteristics. This in-vitro method can be used to evaluate hole size, number, location, and pattern. The rate and volume of an insulin pump's bolus infusion can be correlated with the lateral spread of dye (micrometers from the surface of cannula) at each orifice. In some embodiments, a uniform hole size can produce a reverse the Christmas tree pattern, while a cannula with small, medium, large, and larger hole sizes (proximal to distal) can produce a more uniform cylinder-shaped pattern of delivery. In other embodiments, an optimized uniform hold size can produce a cylinder-shaped pattern. The insulin pump's rate of infusion, however, greatly affects the lateral spread of dye. Rapid bolus infusion produces a wide lateral spread of dye through all orifices. Slow bolus infusion of the same volume produces less lateral spread, because of the lower pressure differential. This in-vitro method produces a low uniform back pressure while the heterogeneous structure of the subcutaneous tissue produces a higher back pressure that may vary at different locations Thus, FIGS. 15A-15B shows a pattern of fluid delivered from a cannula (having holes sizes increasing from the proximal end to the distal end from 0.0005 mm to 0.002") in a triangular (or Christmas tree) pattern. FIGS. 16A-16B show a pattern of fluid delivered from a cannula (having constant holes size of approximately 0.00095") in an inverse triangular (or "upside down Christmas tree") pattern. FIGS. 17A-17C show a pattern of fluid delivered from a cannula (having constant hole size of approximately 0.00075") in a substantially cylindrical pattern. FIGS. 15A-17C show that a cannula with multiple orifices can force insulin into multiple adjacent connective tissue septae, distributing insulin into a greater volume and surface area of adjacent vascular tissue. The multiple orifice cannula produces multiple "finger-like" projections that produce a large surface area in contact with functioning capillary and lymph vessels. Similarly, insulin will flow into multiple connective tissue septae along multiple paths of least resistance. The large surface area of insulin in contact with capillary and lymph vessels will produce more rapid insulin absorption into the circulation (rapid on/off PK-PD).

Further, an observational micro-CT imaging study was performed to compare the distribution patterns of an insulin bolus infused through a commercial CSII catheter relative to the infusion catheters described herein implanted in farm swine for 7 days, 5 days, 3 days, 8 hours, and 10 minutes.

During the study, commercial CSII catheters with a 6 mm Teflon cannula and a single distal orifice (Inset™ Infusion Set, UnoMedical, Denmark) were inserted into the abdomen of two farm swine using aseptic technique. Further, four CSII catheters similar to those described herein were implanted for 7 days, two CSII for 5 days, two CSII for 3 days, two CSII for 8 hours, and two CSII for 10 minutes. A dilute solution of insulin lispro (U-10) was continuously infused through all of the CSII catheters using insulin pumps protected within pockets of a vest (Ping Pump, Animas Corporation, Fraser, Pa.). On the day of excision, a 70 μL bolus of 70% Lispro insulin (U-100) with 30% iodinated contrast agent (diatrizoate, Hypaque 50) was infused through each of the previously inserted CSII catheters using an Animas pump (70 ul infused over 28 seconds). Each CSII catheter and surrounding skin/subcutaneous tissue were excised 5 minutes after the bolus infusion and immediately frozen in isopentane (surrounded by dry ice). Saline and 20% dextrose were infused through an IV catheter to maintain intravascular hydration and to prevent hypoglycemia.

Figure 31:
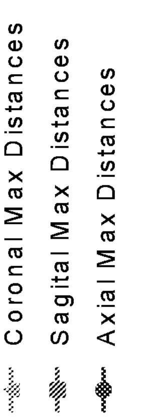
FIG. 31 shows another graph of distribution of fluid relative to the time from catheter insertion.
Figure 31:
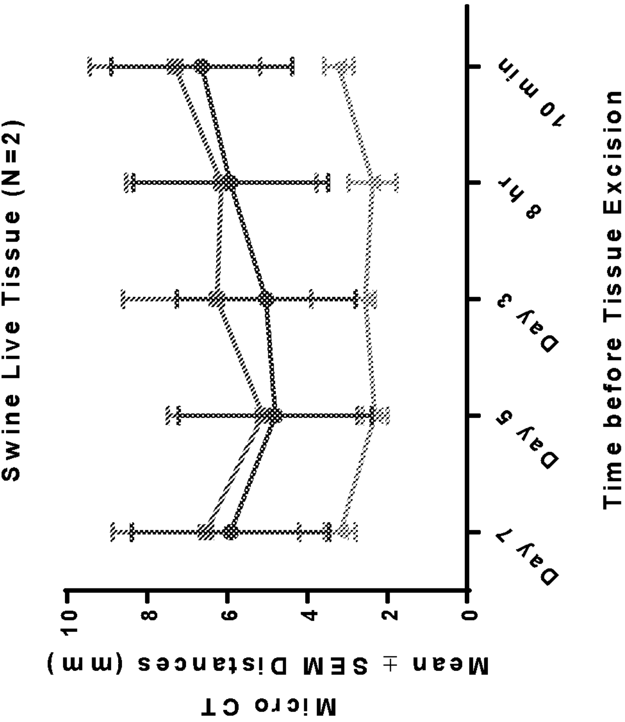

High resolution micro-CT images were recorded using an Inveon Micro-PET/CT Imaging Scanner (Siemens Medical, Germany). Software combined approximately 1,100 scans into 2D and 3D images of the CSII catheter, skin, subcutaneous tissue and the distribution pattern of insulin/contrast agent into the surrounding subcutaneous tissue. RadiAnt DICOM software (version 3.2.3.12921; Medixant, Poznan, Poland) was used to produce quality digital images and measure the distribution pattern of contrast agent in the axial, sagittal, and coronal planes relative to the location of the Teflon cannula tip, 2 mm above the tip and 2 mm below the tip. Distance measurements were recorded for each time point and catheter according to pre-determined criteria for those 3 planes. Mean values were calculated for the 5 time points and the aggregate means of 3 planes are reported. Data are reported as means±SEM. ANOVA with repeated measures was used to examine distribution distances over time and post hoc analysis performed on significant means. $P<0.05$ was set for statistical significance. Exemplary graphs of the results are shown in FIGS. 30 and 31.

During the study, all CSII catheters remained mechanically secured on the skin surface. There were no difficulties with the basal infusion of insulin or the bolus infusion of insulin and x-ray contract agent. Contrast agent typically traveled out of the cannula's orifice into one or more connective tissue planes, parallel to the skin surface. Some contrast agent commonly traveled upward, along the outside of the cannula (path of least resistance) to a more superficial layer, and spread into adjacent connective tissue planes. Contrast migrated to the sub-dermal area in one specimen, and onto the skin surface in another specimen. Data analysis revealed a significant ($p=0.004$) difference in insulin distribution over time. CSII catheters inserted for 7 days and those inserted 10 minutes prior to excision demonstrated more extensive insulin distribution into the surrounding subcutaneous tissues compared to catheters inserted for 3 and 5 days, as shown in FIGS. 30 and 31.

This pilot animal data suggests that the lateral spread of insulin (mm distance away from cannula) at the level of the distal orifice, 2 mm above and 2 mm below the orifice was greatest immediately after implantation. The lateral spread of insulin/dye was decreased from 8 hours to 3 days to 5 days of subcutaneous tissue implantation, perhaps due to an increase in the thickness, density, and continuity of the inflammatory tissue layer. The lateral spread of insulin/dye increased on day 7 of implantation, possibly due to fibrinolysis and partial degradation of the inflammatory tissue layer.

The micro-CT images of an insulin/contrast bolus through a commercial Teflon CSII catheter implanted for 10 minutes to 7 days revealed a highly variable distribution pattern within the adjacent subcutaneous tissue. Insulin/contrast migrated through into adjacent connective tissue planes along the path of least resistance due to the hydrostatic pressure differential. The resistance to flow into adjacent vascular tissue was variable due the heterogeneous anatomy of adipose tissue and the variable density, thickness, and continuity of the surrounding layer of inflammatory tissue. In contrast, the gathered data suggests lower resistance to the lateral spread of insulin/contrast immediately after CSII catheter insertion perhaps due to a lack of inflammation, and after 7 days of CSII implantation perhaps due to fibrinolysis and partial degradation of the surrounding layer of inflammatory tissue. The decreased lateral spread of contrast on day 3 and day 5 of CSII implantation suggests a higher resistance to flow, perhaps due to a dense, thick, and continuous layer of thrombus and inflammatory tissue.

Figure 18:
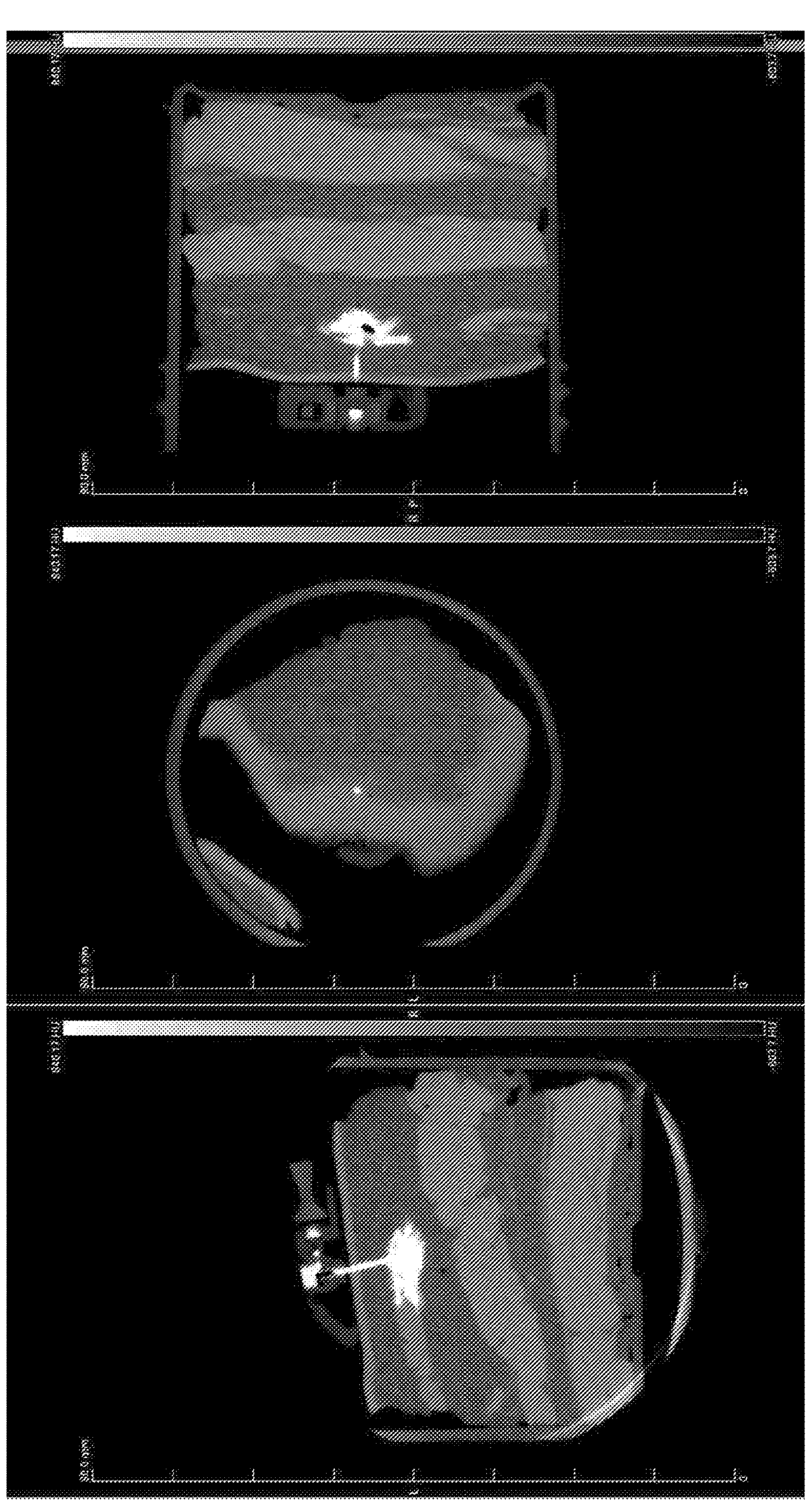
FIG. 18 shows micro-CT images of a commercial CSII catheter attached to the skin surface with a 6 mm Teflon cannula and one distal orifice.
Figure 19:
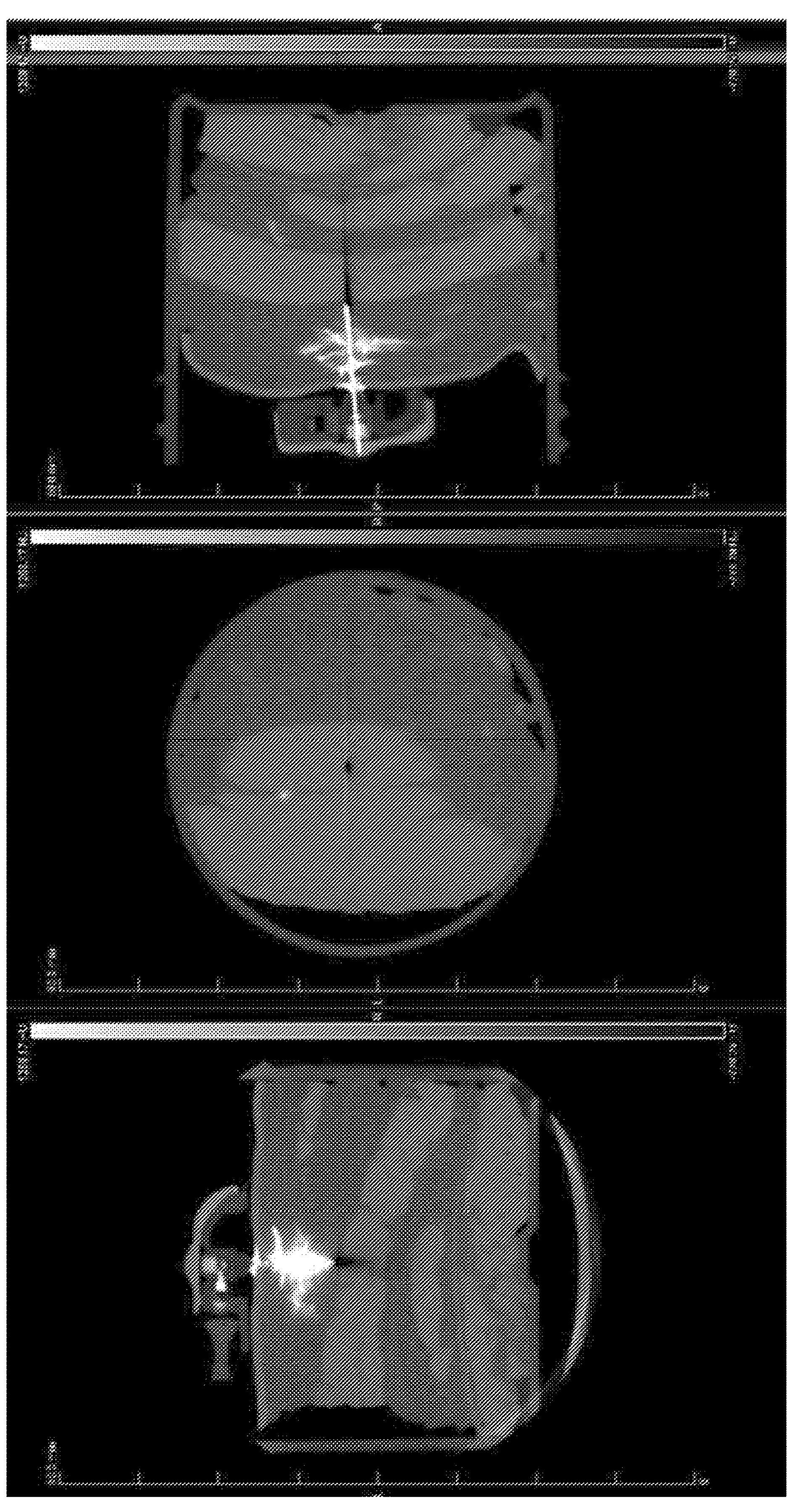
FIG. 19 shows micro-CT images of an a catheter system as described herein attached to the skin surface with a 6 mm stainless steel cannula tipped with a non-traumatic needle and 28 orifices of increasing diameter (proximal to distal)

FIG. 18 shows micro-CT images of a commercial CSII catheter attached to the skin surface with a 6 mm Teflon cannula and one distal orifice. The axial image (left) shows a bright white region of contrast agent within the subcutaneous tissue that surrounds the distal orifice. The insulin/contrast bolus distended the connective tissue septa within the adjacent subcutaneous tissue. The sagittal image (right) shows insulin/contrast spread into the adipose tissue (dark layer above skeletal muscle) and no migration upwards toward the skin surface. The 70 ul insulin depot was concentrated into a small region of vascular tissue with a small surface area. Few finger-like projections were observed that would have increased the surface area in contact with capillary and lymph vessels. In contrast, FIG. 19 shows micro-CT images of an a catheter system as described herein attached to the skin surface with a 6 mm stainless steel cannula tipped with a non-traumatic needle and 28 orifices of increasing diameter (proximal to distal). The skin is thin and light colored, the adipose tissue layer is thicker and darker, and the skeletal muscle layer is deeper and a lighter color. The axial image (left) shows the 70 ul bolus of insulin/contrast traveled into the surrounding subcutaneous tissue in a cylinder-shaped pattern. Multiple finger-like projects of insulin/contrast extended lateral into the adjacent connective tissue septa, to produce a large surface area in contact with capillary and lymph vessels. The sagittal image (right) shows insulin/contrast spread into multiple different planes with the adipose tissue. The 70 ul insulin depot was spread out into a large region of vascular tissue with a large surface area. Numerous finger-like projections of contrast were observed that would have increased the surface area in contact with capillary and lymph vessels.

Thus, a 70 ul bolus of insulin infused through a CSII cannula with one distal orifice tends to significantly distend the adjacent connective tissue fibers enough to distort the tissue. In contrast, a 70 ul bolus of insulin infused through an infusion system described herein with multiple orifices will distend the adjacent connective tissue fibers less and distort the tissue less, leading to improved capillary blood flow and improved lymphatic drainage.

Advantageously, the infusion catheter systems described herein provide safe and effective clinical performance and can be used for ambulatory patients with insulin dependent diabetes (T1DM and end-stage T2DM). The systems can produce rapid and consistent PK-PD for >7 days, facilitating improved automated insulin delivery by a closed-loop AP System. The systems further maintain the blood glucose concentration in the desired range a high percentage of the time and eliminate the risk for hypoglycemia. Further, the system is designed to be inserted using methods that minimize the common failure modes of commercial CSII catheters (improper insertion, obstructed cannula, kinked cannula, dislodged cannula, insulin leakage onto the skin surface, insulin sequestration within layer of inflammatory tissue, and insulin degradation in the wound).

Although often referred to or described herein as CSII catheters for insulin delivery, the infusion catheters described herein can likewise be used for subcutaneous delivery of other medications or fluids. Thus, it should be understood that while the term "insulin" is used throughout, "insulin" can be replaced with any other fluid, medication, or drug.

It should be understood that any feature of one embodiment described herein can be combined with any feature of another. For example, a cannula can include both a vibration mechanism and a heating mechanism.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A continuous subcutaneous insulin-infusion catheter comprising:

- an elongate flexible cannula, the elongate flexible cannula having:
  - a cannula wall;
  - a proximal end configured to be attached to a subcutaneous infusion pump;
  - a distal end configured to be substantially atraumatic;
  - a continuous coiled reinforcing filament made from stainless steel; and
  - a plurality of side holes extending through the cannula wall; and
- an insulin reservoir adapted and configured to couple to and deliver insulin to the elongate flexible cannula;
- wherein the coiled reinforcing filament is configured to prevent the elongate flexible cannula from kinking when inserted into an implantation site;
- wherein the coiled reinforcing filament includes at least 20 turns per millimeter of the cannula;
- wherein the plurality of side holes are arranged in a helical pattern along the axial length of the elongate flexible cannula;
- wherein a longitudinal distance from a proximal-most side hole of the plurality of side holes to a distal-most side hole of the plurality of side holes is approximately 3 to 10 mm.

2. The continuous subcutaneous insulin-infusion catheter of claim 1, wherein the side holes are between 10 μm and 200 μm in diameter.

3. The continuous subcutaneous insulin-infusion catheter system of claim 1, wherein the coiled reinforcing filament has a diameter of 20 μm to 200 μm.

4. The continuous subcutaneous insulin-infusion catheter system of claim 1, wherein a thickness of the cannula wall is between 0.003 inches and 0.01 inches.

5. The continuous subcutaneous insulin-infusion catheter system of claim 1, wherein the coiled reinforcing filament includes at least 30 turns per millimeter of cannula.

6. The continuous subcutaneous insulin-infusion catheter system of claim 1, wherein the coiled reinforcing filament includes at least 40 turns per millimeter of cannula.

7. The continuous subcutaneous insulin-infusion catheter system of claim 1, wherein the elongate flexible cannula is configured to be inserted at a 90 degree angle or a 45 degree angle through epidermis and dermis to a depth of 6-8 mm into subcutaneous tissue.

8. The continuous subcutaneous insulin-infusion catheter system of claim 1, wherein the side holes increase in diameter from the proximal end to the distal end.

9. The continuous subcutaneous insulin-infusion catheter system of claim 1, wherein the elongate flexible cannula is configured to vibrate adjacent subcutaneous tissue.

10. The continuous subcutaneous insulin-infusion catheter system of claim 1, wherein a proximal-most 1 mm to 2 mm portion of the elongate flexible cannula does not include any side holes.

11. The continuous subcutaneous insulin-infusion catheter system of claim 1, wherein the plurality of side holes are configured such that fluid flowing from the elongate flexible cannula through the side holes contacts a lateral surface area of subcutaneous tissue of over 1,000 $\mu m^2$.

12. The continuous subcutaneous insulin-infusion catheter system of claim 1, wherein the proximal-most hole of the plurality of side holes is configured to be positioned greater than 1 mm below a dermis upon insertion of the elongate flexible cannula into subcutaneous tissue.

13. The continuous subcutaneous insulin-infusion catheter system of claim 1, further comprising an inner stylet configured to extend within a lumen of the elongate flexible cannula, the inner stylet having a sharp needle configured to pierce through the epidermis and dermis.

14. The continuous subcutaneous insulin-infusion catheter system of claim 13, further comprising an automatic introducer configured to insert the stylet and elongate flexible cannula into the subcutaneous tissue at a 90 degree angle or a 45 degree angle and to remove the stylet from the lumen of the elongate flexible cannula.

15. The continuous subcutaneous insulin-infusion catheter system of claim 14, wherein the inner stylet is configured to be fully housed within the introducer after removal from the lumen of the elongate flexible cannula for safe disposal.

16. The continuous subcutaneous insulin-infusion catheter system of claim 1, further comprising an introducer configured to insert the elongate flexible cannula through the dermis and subcutaneous tissue at a 90 degree angle or a 45 degree angle, the introducer having a portion configured to retract an inner stylet from the dermis and subcutaneous tissue using a spring mechanism.

17. The continuous subcutaneous insulin-infusion catheter system of claim 1, wherein the plurality of side holes are configured such that the insulin extends 360 degrees around the elongate flexible cannula.

18. The continuous subcutaneous insulin-infusion catheter system of claim 1, further comprising a distal hole at the distal-most tip of the elongate flexible cannula, the distal hole configured to allow fluid to flow therethrough simultaneously with flowing through the plurality of side holes.

19. The continuous subcutaneous insulin-infusion catheter system of claim 1, wherein the elongate flexible cannula is configured to maintain a pressure differential between an inside of the elongate flexible cannula and adjacent subcutaneous tissue when implanted in the subcutaneous tissue that is substantially uniform along an entire length of the elongate flexible cannula.

20. The continuous subcutaneous insulin-infusion catheter system of claim 19, wherein the pressure differential along the entire length of the elongate flexible cannula has a variation within 5-10%.

21. The continuous subcutaneous insulin-infusion catheter system of claim 1, wherein the plurality of side holes are in a distal portion of the elongate flexible cannula, and wherein a proximal portion of the elongate flexible cannula is more flexible than the distal portion.

22. The continuous subcutaneous insulin-infusion catheter system of claim 1, wherein a proximal portion of the elongate flexible cannula is textured to promote adhesion of dermis tissue thereto, the textured proximal portion being configured to produce a localized region of high flow resistance to prevent medication from leaking from the subcutaneous tissue to the skin surface.

23. The continuous subcutaneous insulin-infusion catheter system of claim 1, wherein the elongate flexible cannula is configured to increase flexibility as temperature increases from room temperature to body temperature after implantation.

24. The continuous subcutaneous insulin-infusion catheter system of claim 1, further comprising one or more compounds including a non-steroidal anti-inflammatory compound.

25. The continuous subcutaneous insulin-infusion catheter system of claim 1, further comprising one or more compounds configured to prevent or minimize an acute immune response.

26. The continuous subcutaneous insulin-infusion catheter system of claim 25, wherein the one or more compounds comprise a local anesthetic or a glucocorticoid.

27. The continuous subcutaneous insulin-infusion catheter system of claim 26, wherein:

when the one or more compounds include the local anesthetic, the local anesthetic is lidocaine; or when the one or more compounds include the glucocorticoid, the glucocorticoid is dexamethasone.

28. The continuous subcutaneous insulin-infusion catheter system of claim 1, further comprising:

a platform attached to the elongate flexible cannula, the platform having a bottom surface; and an adhesive patch adapted and configured to contact the bottom surface of the platform and hold the platform to a subject's skin.

29. The continuous subcutaneous insulin-infusion catheter system of claim 28, wherein the elongate flexible cannula is configured to extend from the bottom surface of the platform at an angle that is at least 45° and less than 90°, when the bottom surface of the platform is placed against the surface of the skin.

30. The continuous subcutaneous insulin-infusion catheter system of claim 28, wherein the elongate flexible cannula is configured to extend from the bottom surface of the platform at an angle of 45°, when the bottom surface of the platform is placed against the surface of the skin.

31. The continuous subcutaneous insulin-infusion catheter system of claim 1 further comprising a volume of insulin contained at least in part by the insulin reservoir.

32. The continuous subcutaneous insulin-infusion catheter system of claim 1 further comprising:

a pump configured to produce a positive pressure within the elongate flexible cannula, wherein the reservoir and the pump are configured to deliver insulin to the elongate flexible cannula as a result of the positive pressure.

33. The continuous subcutaneous insulin-infusion catheter system of claim 1 wherein the coiled reinforcing filament is a stainless steel braid center layer.

34. The continuous subcutaneous insulin-infusion catheter system of claim 1 wherein the coiled reinforcing filament is configured to heat up to warm the elongate flexible cannula and adjacent subcutaneous tissue.

35. The continuous subcutaneous insulin-infusion catheter system of claim 1 wherein the coiled reinforcing filament is configured to vibrate the elongate flexible cannula.

36. The continuous subcutaneous insulin-infusion catheter system of claim 1, wherein the plurality of side holes arranged along the helical pattern are in vertical columns having 1 or 2 holes per vertical column; the continuous subcutaneous insulin-infusion catheter system further comprising:

an external platform including:

an infusion set; and a connector;

an elongate flexible tubing extending from the connector to the insulin reservoir and a pump; and an adhesive patch configured to hold the platform to skin.

37. The continuous subcutaneous insulin-infusion catheter system of claim 36, wherein the infusion set is configured to hold a battery and electronics therein.

38. A method of delivering insulin with the continuous subcutaneous infusion catheter system of claim 1 comprising:

inserting the elongate flexible cannula into subcutaneous tissue; and pumping insulin through the plurality of holes such that the insulin spreads to the subcutaneous tissue in a substantially cylindrical pattern along the length of the cannula.

39. A continuous subcutaneous insulin-infusion catheter system, comprising: an elongate flexible cannula, the elongate flexible cannula having a cannula wall and a proximal portion with a proximal end and a distal portion with a distal end, the proximal end configured to be attached to a subcutaneous infusion pump and the distal end configured to be substantially atraumatic when inserted into a subcutaneous tissue, the elongate flexible cannula comprising a coiled reinforcing filament made from stainless steel, wherein the coiled reinforcing filament is configured to prevent the elongate flexible cannula from kinking when inserted into an implantation site; and a plurality of side holes in the distal portion extending through the cannula wall, wherein the plurality of sides holes are arranged in a helical pattern along a length of the cannula wall, wherein a longitudinal distance from a proximal-most side hole to a distal-most side hole is approximately 3 to 10 mm; and an insulin reservoir adapted and configured to couple to and deliver insulin to the elongate flexible cannula;

wherein the coiled reinforcing filament includes at least 20 turns per millimeter of the cannula;

wherein the elongate flexible cannula comprises a polymer configured to increase flexibility as the polymer increases from room temperature to body temperature after implantation;

wherein the proximal portion is more flexible than the distal portion; and wherein the proximal portion is textured to promote adhesion of dermis tissue thereto.

40. The continuous subcutaneous insulin-infusion catheter system of claim 39, wherein the proximal-most hole of the plurality of side holes is configured to be positioned greater than 1 mm below a dermis upon insertion of the elongate flexible cannula into subcutaneous tissue.

41. The continuous subcutaneous insulin-infusion catheter system of claim 40, further comprising:

an inner stylet configured to extend within a lumen of the elongate flexible cannula to pierce through the epidermis and dermis; and an automatic introducer configured to insert the stylet and elongate flexible cannula into the subcutaneous tissue and to remove the stylet from the lumen of the elongate flexible cannula.

42. The continuous subcutaneous insulin-infusion catheter system of claim 39, wherein the plurality of side holes are configured such that the insulin extends 360 degrees around the elongate flexible cannula.

43. The continuous subcutaneous insulin-infusion catheter system of claim 39, further comprising a distal hole at the distal-most tip of the elongate flexible cannula, the elongated flexible cannula configured to allow fluid to flow through the distal hole at the distal-most tip of the elongated cannula and through the plurality of side holes simultaneously.

* * * * *